US005786464A

United States Patent [19]

Seed

[11] Patent Number: 5,786,464

[45] Date of Patent: Jul. 28, 1998

[54] OVEREXPRESSION OF MAMMALIAN AND VIRAL PROTEINS

[75] Inventor: Brian Seed, Boston, Mass.

[73] Assignee: The General Hospital Corporation, Boston, Mass.

[21] Appl. No.: 324,243

[22] Filed: Sep. 19, 1994

[51] Int. Cl.[6] .......................... C12N 15/11; C12N 15/12; C12N 15/48; C12P 19/34

[52] U.S. Cl. ...................... 536/23.5; 435/69.1; 435/91.5; 435/172.3; 435/252.3; 536/23.72

[58] Field of Search .............................. 536/23.5, 23.72; 435/69.1, 172.3, 91.5, 252.3

[56] References Cited

U.S. PATENT DOCUMENTS

| | | | |
|---|---|---|---|
| 4,652,639 | 3/1987 | Stabinsky | 435/91.52 |
| 5,082,767 | 1/1992 | Hatfield et al. | 435/6 |
| 5,270,171 | 12/1993 | Cercek et al. . | |
| 5,276,268 | 1/1994 | Strauch et al. | 800/205 |
| 5,405,776 | 4/1995 | Kotewicz et al. | 435/252.33 |
| 5,464,774 | 11/1995 | Baird et al. | 536/23.51 |

OTHER PUBLICATIONS

Fortkamp, E., et al., DNA, vol. 5, No. 6, "Cloning and expression in Escherichia coli of a synthetic DNA for hirudin, the blood coagulation inhibitor in the leech", pp. 511–517, 1986.

Cohen, J., et al., "Expression of the HIV–1 env (gp160) in the yeast Saccharomyces cerevisiae via expression/secretion vectors and partial characterization of the gene product", in Modern Approaches, New Vaccines, pages 1988.

Chou, K.–C., et al., AIDS Research and Human Retroviruses, vol. 8, No. 12, "Diagrammatization of codon usage in 339 human immunodeficiency virus proteins and its biological implication", pp. 1967–1976, 1992.

Rangwala, S. H., et al., Gene, vol. 122, No. 2, "High–level production of active HIV–1 protease in Escherichia coli", pp. 263–269.

Scorer, C. A., et al., Gene, vol. 136, Nos. 1 & 2, "The intracellular production and secretion of HIV–1 envelope protein in the methylotrophic yeast Picha pastoris", pp. 111–119, 1993.

Holler, T. P., et al., Gene, vol. 136, Nos. 1 & 2, "HIV–1 integrase expressed in Escherichia coli from SyntheticC Gene", PP. 323–328 , 1993.

Bosch, M. L., et al., Journal of Virology, vol. 68, No. 11, "Insertion of N–linked glycosylation sites in the variable regions of the human immunodeficiency virus type–1 surface protein through AAT triplet reiteration", pp. 7566–7569, 1994.

van Hemert, F. J., et al., Journal of Molecular Evolution, vol. 41, No. 2, "The tendency of lentiviral open reading frames to become A–rich: Constraints imposed by viral genome organization and cellular tRNA availability", pp. 132–140, 1995.

Cohen, J., et al., (abstract), in Modern Approaches New Vaccines, "Expression of the HIV–1 env (gp160) in the yeast Saccaromyces cerevisiae via expression/secretion vectors and partial characterization of the gene product", 1988.

Cochrane et al., "Identification and Charaterization of Intragenic Sequences Which Repress Human Immunodeficiency Virus Structural Gene Expression", Journal of Virology, 65(10):5305–5314, (1991).

(List continued on next page.)

*Primary Examiner*—Robert A. Wax
*Assistant Examiner*—William W. Moore
*Attorney, Agent, or Firm*—Clark & Elbing LLP

[57] ABSTRACT

The invention features a synthetic gene encoding a protein normally expressed in mammalian cells wherein at least one non-preferred or less preferred codon in the natural gene encoding the mammalian protein has been replaced by a preferred codon encoding the same amino acid.

18 Claims, 10 Drawing Sheets

```
env   atg aat cca gta ata agt ata aca tta tta tta agt gta tta caa atg agt aga gga caa 60
wt    atg aac cca gtc atc agc atc act ctc ctg ctt tca gtc ttg cag atg tcc cga gga cag
       M   N   P   V   I   S   I   T   L   L   L   S   V   L   Q   M   S   R   G   Q

env   aga gta ata agt tta aca gca tgt tta gta aat caa aat ttg aga tta gat tgt aga cat 120
wt    agg gtg atc agc ctg aca gcc tgc ctg gtg aac cag aac ctt cga ctg gac tgc cgt cat
       R   V   I   S   L   T   A   C   L   V   N   Q   N   L   R   L   D   C   R   H

env   gaa aat aat aca aat ttg cca ata caa cat gaa ttt tca tta acg cgt gaa aaa aaa aaa 180
wt    gag aat aac acc aac ttg ccc atc cag cat gag ttc agc ctg acc cga gag aag aag aag
       E   N   N   T   N   L   P   I   Q   H   E   F   S   L   T   R   E   K   K   K

env   cat gta tta agt gga aca tta gga gta cca gaa cat aca tat aga agt aga gta aat ttg 240
wt    cac gtg ctg tca ggc acc ctg ggg gtt ccc gag cac act tac cgc tcc cgc gtc aac ctt
       H   V   L   S   G   T   L   G   V   P   E   H   T   Y   R   S   R   V   N   L

env   ttt agt gat aga ttc ata aaa gta tta aca tta gca aat ttt aca aca aaa gat gaa gga 300
wt    ttc agt gac cgc ttt atc aag gtc ctt act cta gcc aac ttc acc acc aag gat gag ggc
       F   S   D   R   F   I   K   V   L   T   L   A   N   F   T   T   K   D   E   G

env   gat tat atg tgt gag ctc aga gta agt gga caa aat cca aca agt agt aat aaa aca ata 360
wt    gac tac atg tgt gaa ctt cga gtc tcg ggc cag aat ccc aca agc tcc aat aaa act atc
       D   Y   M   C   E   L   R   V   S   G   Q   N   P   T   S   S   N   K   T   I

env   aat gta ata aga gat aaa tta gta aaa tgt gga gga ata agt tta tta gta caa aat aca 420
wt    aat gtg atc aga gac aag ctg gtc aag tgt ggt ggc ata agc ctg ctg gtt caa aac act
       N   V   I   R   D   K   L   V   K   C   G   G   I   S   L   L   V   Q   N   T

env   agt tgg tta tta tta tta tta tta agt tta agt ttt tta caa gca aca gat ttt ata agt 480
wt    tcc tgg ctg ctg ctg ctc ctg ctt tcc ctc tcc ttc ctc caa gcc acg gac ttc att tct
       S   W   L   L   L   L   L   L   S   L   S   F   L   Q   A   T   D   F   I   S

env   tta tga   486        (SEQ ID NO: 36)
wt    ctg tga              (SEQ ID NO: 37)
       L   *
```

OTHER PUBLICATIONS

D'Agostino et al., "The Rev Protein of Human Immunodeficiency Virus Type 1 Promotes Polysomal Association and Translation of gag/pol and vpu/env mRNAs", Molucular and Cellular Biology, 12(3):1375–1386, (1992).

Feinberg et al., "HTLV-III Expression and Production Involve Complex Regulation at the Levels of Splicing and Translation of Viral RNA", Cell, 46:807–817, (1986).

Hammarskjold et al., "Regulation of Human Immunodeficiency Virus env Expression by the rev Gene Product"Journal of Virology, 63(5):1959–1966, (1989).

Nakamura et al., "Two types of linkage between codon usage and gene-expression levels", *FEBS LETTERS*, 289(1):123–125, (1991).

Robinson et al., "Codon usage can affect efficiency of translation of genes in *Escherichia coli*", Nucleic Acids Research, 12(17):6663–6671, (1984).

Zhang et al., "Low-usage codons in *Escherichia coli*, yeast, fruit fly and primates", Gene, 105(1):61–72 (1991).

Zhang et al., "Graphic Analysis of Codon Usage Strategy in 1490 Human Proteins", Journal of Protein Chemistry, 12(3):329–335, (1993).

Coulombe and Skup, Gene 46:89–95 (1986).

Kamiya et al., Jpn J. Cancer Res. 80:200–203 (1989).

McCarrey, Nucleic Acids Res. 18:949–955 (1990).

Newgard et al., Proc. Natl. Acad. Sci. USA 83:8132–8136 (1986).

Sharp et al., Nucleic Acids Res. 16:8207–8211 (1988).

Inouye et al., FEBS Letters 341:277–280 (1994).

Hernan et al., Biochemistry 31:861908628 (1992).

Williams et al., Nucleic Acids Research 16:10453–10467 (1988).

Syngp120mn

```
   1 CTCGAGATCC ATTGTGCTCT AAAGGAGATA CCCGGCCAGA CACCCTCACC
  51 TGCGGTGCCC AGCTGCCCAG GCTGAGGCAA GAGAAGGCCA GAAACCATGC
 101 CCATGGGGTC TCTGCAACCG CTGGCCACCT TGTACCTGCT GGGGATGCTG
 151 GTCGCTTCCG TGCTAGCCAC CGAGAAGCTG TGGGTGACCG TGTACTACGG
 201 CGTGCCCGTG TGGAAGGAGG CCACCACCAC CCTGTTCTGC GCCAGCGACG
 251 CCAAGGCGTA CGACACCGAG GTGCACAACG TGTGGGCCAC CCAGGCGTGC
 301 GTGCCCACCG ACCCCAACCC CCAGGAGGTG GAGCTCGTGA ACGTGACCGA
 351 GAACTTCAAC ATGTGGAAGA ACAACATGGT GGAGCAGATG CATGAGGACA
 401 TCATCAGCCT GTGGGACCAG AGCCTGAAGC CCTGCGTGAA GCTGACCCCC
 451 CTGTGCGTGA CCCTGAACTG CACCGACCTG AGGAACACCA CCAACACCAA
 501 CAACAGCACC GCCAACAACA ACAGCAACAG CGAGGGCACC ATCAAGGGCG
 551 GCGAGATGAA GAACTGCAGC TTCAACATCA CCACCAGCAT CCGCGACAAG
 601 ATGCAGAAGG AGTACGCCCT GCTGTACAAG CTGGATATCG TGAGCATCGA
 651 CAACGACAGC ACCAGCTACC GCCTGATCTC CTGCAACACC AGCGTGATCA
 701 CCCAGGCCTG CCCCAAGATC AGCTTCGAGC CCATCCCCAT CCACTACTGC
 751 GCCCCCGCCG GCTTCGCCAT CCTGAAGTGC AACGACAAGA AGTTCAGCGG
 801 CAAGGGCAGC TGCAAGAACG TGAGCACCGT GCAGTGCACC CACGGCATCC
 851 GGCCGGTGGT GAGCACCCAG CTCCTGCTGA ACGGCAGCCT GGCCGAGGAG
 901 GAGGTGGTGA TCCGCAGCGA GAACTTCACC GACAACGCCA AGACCATCAT
 951 CGTGCACCTG AATGAGAGCG TGCAGATCAA CTGCACGCGT CCCAACTACA
1001 ACAAGCGCAA GCGCATCCAC ATCGGCCCCG GGCGCGCCTT CTACACCACC
1051 AAGAACATCA TCGGCACCAT CCGCCAGGCC CACTGCAACA TCTCTAGAGC
1101 CAAGTGGAAC GACACCCTGC GCCAGATCGT GAGCAAGCTG AAGGAGCAGT
1151 TCAAGAACAA GACCATCGTG TTCAACCAGA GCAGCGGCGG CGACCCCGAG
1201 ATCGTGATGC ACAGCTTCAA CTGCGGCGGC GAATTCTTCT ACTGCAACAC
1251 CAGCCCCCTG TTCAACAGCA CCTGGAACGG CAACAACACC TGGAACAACA
1301 CCACCGGCAG CAACAACAAT ATTACCCTCC AGTGCAAGAT CAAGCAGATC
1351 ATCAACATGT GGCAGGAGGT GGGCAAGGCC ATGTACGCCC CCCCCATCGA
1401 GGGCCAGATC CGGTGCAGCA GCAACATCAC CGGTCTGCTG CTGACCCGCG
1451 ACGGCGGCAA GGACACCGAC ACCAACGACA CCGAAATCTT CCGCCCCGGC
```

Fig. 1A

```
1501 GGCGGCGACA TGCGCGACAA CTGGAGATCT GAGCTGTACA AGTACAAGGT
1551 GGTGACGATC GAGCCCCTGG GCGTGGCCCC CACCAAGGCC AAGCGCCGCG
1601 TGGTGCAGCG CGAGAAGCGC TAAAGCGGCC GC          (SEQ ID NO: 34)
```

Fig. 1B

Syngp160mn

```
   1 ACCGAGAAGC TGTGGGTGAC CGTGTACTAC GGCGTGCCCG TGTGGAAGGA
  51 GGCCACCACC ACCCTGTTCT GCGCCAGCGA CGCCAAGGCG TACGACACCG
 101 AGGTGCACAA CGTGTGGGCC ACCCAGGCGT GCGTGCCCAC CGACCCCAAC
 151 CCCCAGGAGG TGGAGCTCGT GAACGTGACC GAGAACTTCA ACATGTGGAA
 201 GAACAACATG GTGGAGCAGA TGCATGAGGA CATCATCAGC CTGTGGGACC
 251 AGAGCCTGAA GCCCTGCGTG AAGCTGACCC CCCTGTGCGT GACCCTGAAC
 301 TGCACCGACC TGAGGAACAC CACCAACACC AACAACAGCA CCGCCAACAA
 351 CAACAGCAAC AGCGAGGGCA CCATCAAGGG CGGCGAGATG AAGAACTGCA
 401 GCTTCAACAT CACCACCAGC ATCCGCGACA AGATGCAGAA GGAGTACGCC
 451 CTGCTGTACA AGCTGGATAT CGTGAGCATC GACAACGACA GCACCAGCTA
 501 CCGCCTGATC TCCTGCAACA CCAGCGTGAT CACCCAGGCC TGCCCCAAGA
 551 TCAGCTTCGA GCCCATCCCC ATCCACTACT GCGCCCCCGC CGGCTTCGCC
 601 ATCCTGAAGT GCAACGACAA GAAGTTCAGC GGCAAGGGCA GCTGCAAGAA
 651 CGTGAGCACC GTGCAGTGCA CCCACGGCAT CCGGCCGGTG GTGAGCACCC
 701 AGCTCCTGCT GAACGGCAGC CTGGCCGAGG AGGAGGTGGT GATCCGCAGC
 751 GAGAACTTCA CCGACAACGC CAAGACCATC ATCGTGCACC TGAATGAGAG
 801 CGTGCAGATC AACTGCACGC GTCCCAACTA CAACAAGCGC AAGCGCATCC
 851 ACATCGGCCC CGGGCGCGCC TTCTACACCA CCAAGAACAT CATCGGCACC
 901 ATCCGCCAGG CCCACTGCAA CATCTCTAGA GCCAAGTGGA ACGACACCCT
 951 GCGCCAGATC GTGAGCAAGC TGAAGGAGCA GTTCAAGAAC AAGACCATCG
1001 TGTTCAACCA GAGCAGCGGC GGCGACCCCG AGATCGTGAT GCACAGCTTC
1051 AACTGCGGCG GCGAATTCTT CTACTGCAAC ACCAGCCCCC TGTTCAACAG
1101 CACCTGGAAC GGCAACAACA CCTGGAACAA CACCACCGGC AGCAACAACA
1151 ATATTACCCT CCAGTGCAAG ATCAAGCAGA TCATCAACAT GTGGCAGGAG
1201 GTGGGCAAGG CCATGTACGC CCCCCCCATC GAGGGCCAGA TCCGGTGCAG
1251 CAGCAACATC ACCGGTCTGC TGCTGACCCG CGACGGCGGC AAGGACACCG
1301 ACACCAACGA CACCGAAATC TTCCGCCCCG GCGGCGGCGA CATGCGCGAC
1351 AACTGGAGAT CTGAGCTGTA CAAGTACAAG GTGGTGACGA TCGAGCCCCT
1401 GGGCGTGGCC CCCACCAAGG CCAAGCGCCG CGTGGTGCAG CGCGAGAAGC
1451 GGGCCGCCAT CGGCGCCCTG TTCCTGGGCT TCCTGGGGGC GGCGGGCAGC
```

Fig. 1C

1501 ACCATGGGGG CCGCCAGCGT GACCCTGACC GTGCAGGCCC GCCTGCTCCT
1551 GAGCGGCATC GTGCAGCAGC AGAACAACCT CCTCCGCGCC ATCGAGGCCC
1601 AGCAGCATAT GCTCCAGCTC ACCGTGTGGG GCATCAAGCA GCTCCAGGCC
1651 CGCGTGCTGG CCGTGGAGCG CTACCTGAAG GACCAGCAGC TCCTGGGCTT
1701 CTGGGGCTGC TCCGGCAAGC TGATCTGCAC CACCACGGTA CCCTGGAACG
1751 CCTCCTGGAG CAACAAGAGC CTGGACGACA TCTGGAACAA CATGACCTGG
1801 ATGCAGTGGG AGCGCGAGAT CGATAACTAC ACCAGCCTGA TCTACAGCCT
1851 GCTGGAGAAG AGCCAGACCC AGCAGGAGAA GAACGAGCAG GAGCTGCTGG
1901 AGCTGGACAA GTGGGCGAGC CTGTGGAACT GGTTCGACAT CACCAACTGG
1951 CTGTGGTACA TCAAAATCTT CATCATGATT GTGGGCGGCC TGGTGGGCCT
2001 CCGCATCGTG TTCGCCGTGC TGAGCATCGT GAACCGCGTG CGCCAGGGCT
2051 ACAGCCCCCT GAGCCTCCAG ACCCGGCCCC CCGTGCCGCG CGGGCCCGAC
2101 CGCCCCGAGG GCATCGAGGA GGAGGGCGGC GAGCGCGACC GCGACACCAG
2151 CGGCAGGCTC GTGCACGGCT TCCTGGCGAT CATCTGGGTC GACCTCCGCA
2201 GCCTGTTCCT GTTCAGCTAC CACCACCGCG ACCTGCTGCT GATCGCCGCC
2251 CGCATCGTGG AACTCCTAGG CCGCCGCGGC TGGGAGGTGC TGAAGTACTG
2301 GTGGAACCTC CTCCAGTATT GGAGCCAGGA GCTGAAGTCC AGCGCCGTGA
2351 GCCTGCTGAA CGCCACCGCC ATCGCCGTGG CCGAGGGCAC CGACCGCGTG
2401 ATCGAGGTGC TCCAGAGGGC CGGGAGGGCG ATCCTGCACA TCCCCACCCG
2451 CATCCGCCAG GGGCTCGAGA GGGCGCTGCT G (SEQ ID NO: 35)

Fig. 1D

```
env  atg aat cca gta ata agt ata aca tta tta tta agt gta tta caa atg agt aga gga caa  60
wt   atg aac cca gtc atc agc atc act ctc ctg ctt tca gtc ttg cag atg tcc cga gga cag
      M   N   P   V   I   S   I   T   L   L   L   S   V   L   Q   M   S   R   G   Q

env  aga gta ata agt tta aca gca tgt tta gta aat caa aat ttg aga tta gat tgt aga cat 120
wt   agg gtg atc agc ctg aca gcc tgc ctg gtg aac cag aac ctt cga ctg gac tgc cgt cat
      R   V   I   S   L   T   A   C   L   V   N   Q   N   L   R   L   D   C   R   H

env  gaa aat aat aca aat ttg cca ata caa cat gaa ttt tca tta acg cgt gaa aaa aaa aaa 180
wt   gag aat aac acc aac ttg ccc atc cag cat gag ttc agc ctg acc cga gag aag aag aag
      E   N   N   T   N   L   P   I   Q   H   E   F   S   L   T   R   E   K   K   K

env  cat gta tta agt gga aca tta gga gta cca gaa cat aca tat aga agt aga gta aat ttg 240
wt   cac gtg ctg tca ggc acc ctg ggg gtt ccc gag cac act tac cgc tcc cgc gtc aac ctt
      H   V   L   S   G   T   L   G   V   P   E   H   T   Y   R   S   R   V   N   L

env  ttt agt gat aga ttc ata aaa gta tta aca tta gca aat ttt aca aca aaa gat gaa gga 300
wt   ttc agt gac cgc ttt atc aag gtc ctt act cta gcc aac ttc acc acc aag gat gag ggc
      F   S   D   R   F   I   K   V   L   T   L   A   N   F   T   T   K   D   E   G

env  gat tat atg tgt gag ctc aga gta agt gga caa aat cca aca agt agt aat aaa aca ata 360
wt   gac tac atg tgt gaa ctt cga gtc tcg ggc cag aat ccc aca agc tcc aat aaa act atc
      D   Y   M   C   E   L   R   V   S   G   Q   N   P   T   S   S   N   K   T   I

env  aat gta ata aga gat aaa tta gta aaa tgt gga gga ata agt tta tta gta caa aat aca 420
wt   aat gtg atc aga gac aag ctg gtc aag tgt ggt ggc ata agc ctg ctg gtt caa aac act
      N   V   I   R   D   K   L   V   K   C   G   G   I   S   L   L   V   Q   N   T

env  agt tgg tta tta tta tta tta tta agt tta agt ttt tta caa gca aca gat ttt ata agt 480
wt   tcc tgg ctg ctg ctg ctc ctg ctt tcc ctc tcc ttc ctc caa gcc acg gac ttc att tct
      S   W   L   L   L   L   L   L   S   L   S   F   L   Q   A   T   D   F   I   S

env  tta tga  486       (SEQ ID NO: 36)
wt   ctg tga            (SEQ ID NO: 37)
      L   *
```

Fig. 6

OVEREXPRESSION OF MAMMALIAN AND VIRAL PROTEINS

This invention was made with Government support under Contract #AI27849 and DK43031 awarded by the National Institutes of Health. The Government has certain rights in this invention.

FIELD OF THE INVENTION

The invention concerns genes and methods for expressing eukaryotic and viral proteins at high levels in eukaryotic cells.

BACKGROUND OF THE INVENTION

Expression of eukaryotic gene products in prokaryotes is sometimes limited by the presence of codons that are infrequently used in *E. coli*. Expression of such genes can be enhanced by systematic substitution of the endogenous codons with codons overrepresented in highly expressed prokaryotic genes (Robinson et al. 1984). It is commonly supposed that rare codons cause pausing of the ribosome, which leads to a failure to complete the nascent polypeptide chain and an uncoupling of transcription and translation. The mRNA 3' end of the stalled ribosome is exposed to cellular ribonucleases, which decreases the stability of the transcript.

SUMMARY OF THE INVENTION

The invention features a synthetic gene encoding a protein normally expressed in mammalian cells wherein at least one non-preferred or less preferred codon in the natural gene encoding the mammalian protein has been replaced by a preferred codon encoding the same amino acid.

Preferred codons are: Ala (gcc); Arg (cgc); Asn (aac); Asp (gac) Cys (tgc); Gln (cag); Gly (ggc); His (cac); Ile (atc); Leu (ctg); Lys (aag); Pro (ccc); Phe (ttc); Ser (agc); Thr (acc); Tyr (tac); and Val (gtg). Less preferred codons are: Gly (ggg); Ile (att); Leu (ctc); Ser (tcc); Val (gtc). All codons which do not fit the description of preferred codons or less preferred codons are non-preferred codons.

By "protein normally expressed in mammalian cells" is meant a protein which is expressed in mammalian cells under natural conditions. The term includes genes in the mammalian genome encoding polypeptides such as Factor VIII, Factor IX, interleukins, and other proteins. The term also includes genes which are expressed in a mammalian cell under disease conditions such as oncogenes as well as genes which are encoded by a virus (including a retrovirus) which are expressed in mammalian cells post-infection In preferred embodiments, the synthetic gene is capable of expressing said mammalian protein at a level which is at least 110%, 150%, 200%, 500%, 1,000%, or 10,000% of that expressed by said natural gene in an in vitro mammalian cell culture system under identical conditions (i.e., same cell type, same culture conditions, same expression vector).

Suitable cell culture systems for measuring expression of the synthetic gene and corresponding natural gene are described below. Other suitable expression systems employing mammalian cells are well known to those skilled in the art and are described in, for example, the standard molecular biology reference works noted below. Vectors suitable for expressing the synthetic and natural genes are described below and in the standard reference works described below. By "expression" is meant protein expression. Expression can be measured using an antibody specific for the protein of interest. Such antibodies and measurement techniques are well known to those skilled in the art. By "natural gene" is meant the gene sequence which naturally encodes the protein.

In other preferred embodiments at least 10%, 20%, 30%, 40%, 50%, 60%, 70%, 80%, or 90% of the codons in the natural gene are non-preferred codons.

In a preferred embodiment the protein is a retroviral protein. In a more preferred embodiment the protein is a lentiviral protein. In an even more preferred embodiment the protein is an HIV protein. In other preferred embodiments the protein is gag, pol, env, gp120, or gp160. In other preferred embodiments the protein is a human protein.

The invention also features a method for preparing a synthetic gene encoding a protein normally expressed by mammalian cells. The method includes identifying non-preferred and less-preferred codons in the natural gene encoding the protein and replacing one or more of the non-preferred and less-preferred codons with a preferred codon encoding the same amino acid as the replaced codon.

Under some circumstances (e.g., to permit introduction of a restriction site) it may be desirable to replace a non-preferred codon with a less preferred codon rather than a preferred codon.

It is not necessary to replace all less preferred or non-preferred codons with preferred codons. Increased expression can be accomplished even with partial replacement.

In other preferred embodiments the invention features vectors (including expression vectors) comprising the synthetic gene.

By "vector" is meant a DNA molecule, derived, e.g., from a plasmid, bacteriophage, or mammalian or insect virus, into which fragments of DNA may be inserted or cloned. A vector will contain one or more unique restriction sites and may be capable of autonomous replication in a defined host or vehicle organism such that the cloned sequence is reproducible. Thus, by "expression vector" is meant any autonomous element capable of directing the synthesis of a protein. Such DNA expression vectors include mammalian plasmids and viruses.

The invention also features synthetic gene fragments which encode a desired portion of the protein. Such synthetic gene fragments are similar to the synthetic genes of the invention except that they encode only a portion of the protein. Such gene fragments preferably encode at least 50, 100, 150, or 500 contiguous amino acids of the protein.

In constructing the synthetic genes of the invention it may be desirable to avoid CpG sequences as these sequences may cause gene silencing.

The codon bias present in the HIV gp120 envelope gene is also present in the gag and pol proteins. Thus, replacement of a portion of the non-preferred and less preferred codons found in these genes with preferred codons should produce a gene capable of higher level expression. A large fraction of the codons in the human genes encoding Factor VIII and Factor IX are non-preferred codons or less preferred codons. Replacement of a portion of these codons with preferred codons should yield genes capable of higher level expression in mammalian cell culture. Conversely, it may be desirable to replace preferred codons in a naturally occurring gene with less-preferred codons as a means of lowering expression.

Standard reference works describing the general principles of recombinant DNA technology include Watson, J. D. et al., *Molecular Biology of the Gene*, Volumes I and II, the Benjamin/Cummings Publishing Company, Inc., publisher, Menlo Park, Calif. (1987); Darnell, J. E. et al., *Molecular Cell Biology*, Scientific American Books, Inc., Publisher, New York, N.Y. (1986); Old, R. W., et al., *Principles of Gene Manipulation: An Introduction to Genetic Engineering*, 2d edition, University of California Press, publisher, Berkeley, Calif. (1981); Maniatis, T., et al., *Molecular Cloning: A Laboratory Manual*, 2nd Ed. Cold Spring Harbor Laboratory, publisher, Cold Spring Harbor, N.Y. (1989); and *Current Protocols in Molecular Biology*, Ausubel et al., Wiley Press, New York, N.Y. (1989).

DETAILED DESCRIPTION

Description of the Drawings

FIG. 1 depicts the sequence of the synthetic gp120 and a synthetic gp160 gene in which codons have been replaced by those found in highly expressed human genes.

FIG. 5, panel B is a shorter exposure of a similar experiment in which syngp120mnrre was cotransfected with or without pCMVrev. FIG. 5, panel C is a schematic diagram of the constructs used in panel A.

FIG. 6 is a comparison of the sequence of the wildtype rat THY-1 gene (wt) and a synthetic rat THY-1 gene (env) constructed by chemical synthesis and having the most prevalent codons found in the HIV-1 env gene.

FIG. 9, panel B is a schematic diagram of the constructs used in the experiment depicted in panel A of this figure.

DESCRIPTION OF THE PREFERRED EMBODIMENTS

Figure 2:
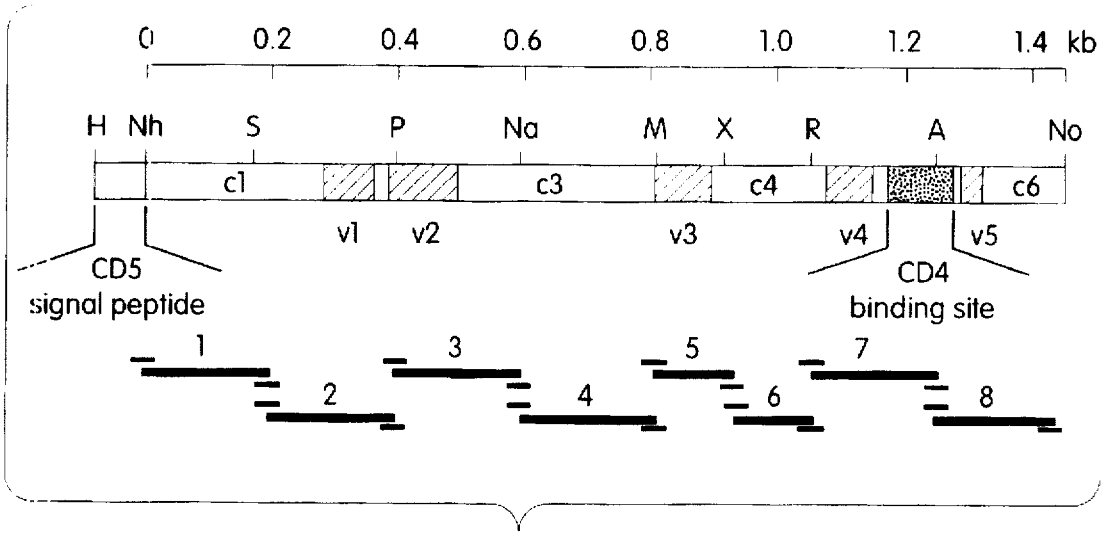
FIG. 2 is a schematic drawing of the synthetic gp120 (HIV-1 MN) gene. The shaded portions marked v1 to v5 indicate hypervariable regions. The filled box indicates the CD4 binding site. A limited number of the unique restriction sites ares shown: H (Hind3), Nh (Nhe1), P (Pst1), Na (Nae1), M (Mlu1), R (EcoR1), A (Age1) and No (Not1). The chemically synthesized DNA fragments which served as PCR templates are shown below the gp120 sequence, along with the locations of the primers used for their amplification.

Construction of a Synthetic gp120 Gene Having Codons Found in Highly Expressed Human Genes A codon frequency table for the envelope precursor of the LAV subtype of HIV-1 was generated using software developed by the University of Wisconsin Genetics Computer Group. The results of that tabulation are contrasted in Table 1 with the pattern of codon usage by a collection of highly expressed human genes. For any amino acid encoded by degenerate codons, the most favored codon of the highly expressed genes is different from the most favored codon of the HIV envelope precursor. Moreover a simple rule describes the pattern of favored envelope codons wherever it applies: preferred codons maximize the number of adenine residues in the viral RNA. In all cases but one this means that the codon in which the third position is A is the most frequently used. In the special case of serine, three codons equally contribute one A residue to the mRNA; together these three comprise 85% of the codons actually used in envelope transcripts. A particularly striking example of the A bias is found in the codon choice for arginine, in which the AGA triplet comprises 88% of all codons. In addition to the preponderance of A residues, a marked preference is seen for uridine among degenerate codons whose third residue must be a pyrimidine. Finally, the inconsistencies among the less frequently used variants can be accounted for by the observation that the dinucleotide CpG is underrepresented; thus the third position is less likely to be G whenever the second position is C, as in the codons for alanine, proline, serine and threonine; and the CGX triplets for arginine are hardly used at all.

TABLE 1

Codon Frequency in the HIV-1 IIIb env gene and in highly expressed human genes.

| | | High | Env |
|---|---|---|---|
| Ala | | | |
| GC | C | 53 | 27 |
| | T | 17 | 18 |
| | A | 13 | 50 |
| | G | 17 | 5 |
| Arg | | | |
| CG | C | 37 | 0 |
| | T | 7 | 4 |
| | A | 6 | 0 |
| | G | 21 | 0 |
| AG | A | 10 | 88 |
| | G | 18 | 8 |
| Asn | | | |
| AA | C | 78 | 30 |
| | T | 22 | 70 |
| Asp | | | |
| GA | C | 75 | 33 |
| | T | 25 | 67 |
| Leu | | | |
| CT | C | 26 | 10 |
| | T | 5 | 7 |
| | A | 3 | 17 |
| | G | 58 | 17 |
| TT | A | 2 | 30 |
| | G | 6 | 20 |
| Lys | | | |
| AA | A | 18 | 68 |
| | G | 82 | 32 |
| Pro | | | |
| CC | C | 48 | 27 |
| | T | 19 | 14 |
| | A | 16 | 55 |
| | G | 17 | 5 |
| Phe | | | |
| TT | C | 80 | 26 |
| | T | 20 | 74 |
| Cys | | | |
| TG | C | 68 | 16 |
| | T | 32 | 84 |
| Gln | | | |
| CA | A | 12 | 55 |
| | G | 88 | 45 |
| Glu | | | |
| GA | A | 25 | 67 |
| | G | 75 | 33 |

TABLE 1-continued

Codon Frequency in the HIV-1 IIIb env gene and in highly expressed human genes.

| | | High | Env |
|---|---|---|---|
| Gly | | | |
| GG | C | 50 | 6 |
| | T | 12 | 13 |
| | A | 14 | 53 |
| | G | 24 | 28 |
| His | | | |
| CA | C | 79 | 25 |
| | T | 21 | 75 |
| Ile | | | |
| AT | C | 77 | 25 |
| | T | 18 | 31 |
| | A | 5 | 44 |
| Ser | | | |
| TC | C | 28 | 8 |
| | T | 13 | 8 |
| | A | 5 | 22 |
| | G | 9 | 0 |
| AG | C | 34 | 22 |
| | T | 10 | 41 |
| Thr | | | |
| AC | C | 57 | 20 |
| | T | 14 | 22 |
| | A | 14 | 51 |
| | G | 15 | 7 |
| Tyr | | | |
| TA | C | 74 | 8 |
| | T | 26 | 92 |
| Val | | | |
| GT | C | 25 | 12 |
| | T | 7 | 9 |
| | A | 5 | 62 |
| | G | 64 | 18 |

Codon frequency was calculated using the GCG program established the the University of Wisconsin Genetics Computer Group. Numbers represent the percentage of cases in which the particular codon is used. Codon usage frequencies of envelope genes of other HIV-1 virus isolates are comparable and show a similar bias.

In order to produce a gp120 gene capable of high level expression in mammalian cells, a synthetic gene encoding the gp120 segment of HIV-1 was constructed (syngp120mn), based on the sequence of the most common North American subtype, HIV-1 MN (Shaw et al. 1984; Gallo et al. 1986). In this synthetic gp120 gene nearly all of the native codons have been systematically replaced with codons most frequently used in highly expressed human genes (FIG. 1). This synthetic gene was assembled from chemically synthesized oligonucleotides of 150 to 200 bases in length. If oligonucleotides exceeding 120 to 150 bases are chemically synthesized, the percentage of full-length product can be low, and the vast excess of material consists of shorter oligonucleotides. Since these shorter fragments inhibit cloning and PCR procedures, it can be very difficult to use oligonucleotides exceeding a certain length. In order to use crude synthesis material without prior purification, single-stranded oligonucleotide pools were PCR amplified before cloning. PCR products were purified in agarose gels and used as templates in the next PCR step. Two adjacent fragments could be co-amplified because of overlapping sequences at the end of either fragment. These fragments, which were between 350 and 400 bp in size, were subcloned into a pCDM7-derived plasmid containing the leader sequence of the CD5 surface molecule followed by a Nhe1/Pst1/Mlu1/EcoR1/BamH1 polylinker. Each of the restriction enzymes in this polylinker represents a site that is present at either the 5' or 3' end of the PCR-generated fragments. Thus, by sequential subcloning of each of the 4 long fragments, the whole gp120 gene was assembled. For each fragment 3 to 6 different clones were subcloned and sequenced prior to assembly. A schematic drawing of the method used to construct the synthetic gp120 is shown in FIG. 2. The sequence of the synthetic gp120 gene (and a synthetic gp160 gene created using the same approach) is presented in FIG. 1.

The mutation rate was considerable. The most commonly found mutations were short (1 nucleotide) and long (up to 30 nucleotides) deletions. In some cases it was necessary to exchange parts with either synthetic adapters or pieces from other subclones without mutation in that particular region. Some deviations from strict adherence to optimized codon usage were made to accommodate the introduction of restriction sites into the resulting gene to facilitate the replacement of various segments (FIG. 2). These unique restriction sites were introduced into the gene at approximately 100 bp intervals. The native HIV leader sequence was exchanged with the highly efficient leader peptide of the human CD5 antigen to facilitate secretion. The plasmid used for construction is a derivative of the mammalian expression vector pCDM7 transcribing the inserted gene under the control of a strong human CMV immediate early promoter.

To compare the wild-type and synthetic gp120 coding sequences, the synthetic gp120 coding sequence was inserted into a mammalian expression vector and tested in transient transfection assays. Several different native gp120 genes were used as controls to exclude variations in expression levels between different virus isolates and artifacts induced by distinct leader sequences. The gp120 HIV IIIb construct used as control was generated by PCR using a Sal1/Xho1 HIV-1 HXB2 envelope fragment as template. To exclude PCR induced mutations a Kpn1/Ear1 fragment containing approximately 1.2 kb of the gene was exchanged with the respective sequence from the proviral clone. The wildtype gp120mn constructs used as controls were cloned by PCR from HIV-1 MN infected C8166 cells (AIDS Repository, Rockville, Md.) and expressed gp120 either with a native envelope or a CD5 leader sequence. Since proviral clones were not available in this case, two clones of each construct were tested to avoid PCR artifacts. To determine the amount of secreted gp120 semi-quantitatively supernatants of 293T cells transiently transfected by calcium phosphate coprecipitation were immunoprecipitated with soluble CD4:immunoglobulin fusion protein and protein A sepharose.

Figure 3:
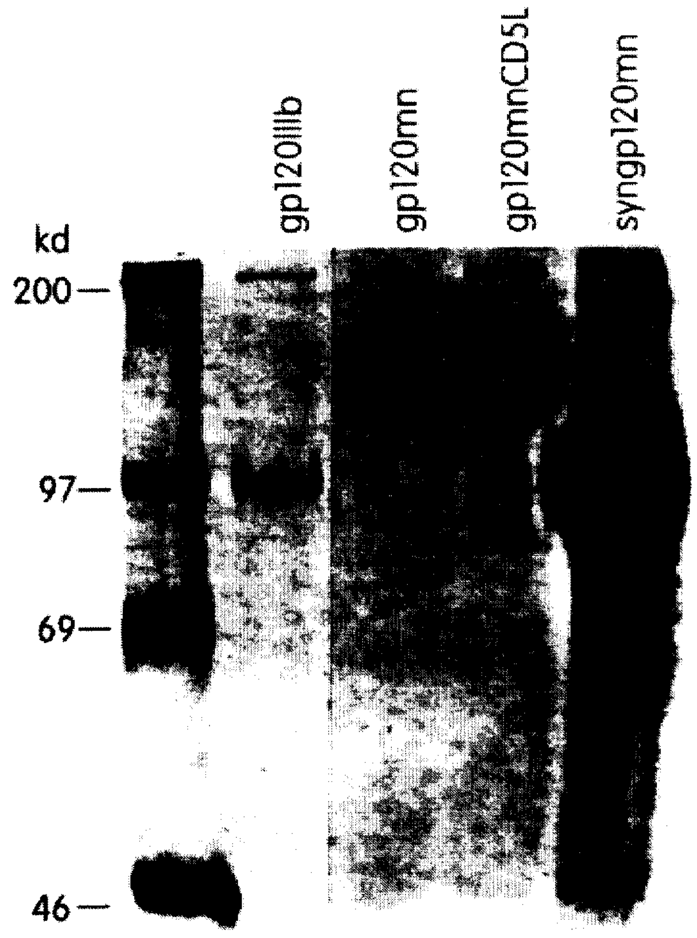
FIG. 3 is a photograph of the results of transient transfection assays used to measure gp120 expression. Gel electrophoresis of immunoprecipitated supernatants of 293T cells transfected with plasmids expressing gp120 encoded by the IIIB isolate of HIV-1 (gp120IIIb), by the MN isolate (gp120mn), by the MN isolate modified by substitution of the endogenous leader peptide with that of the CD5 antigen (gp120mnCD5L), or by the chemically synthesized gene encoding the MN variant with the human CD5Leader (syngp120mn). Supernatants were harvested following a 12 hour labeling period 60 hours post-transfection and immunoprecipitated with CD4:IgG1 fusion protein and protein A sepharose.

The results of this analysis (FIG. 3) show that the synthetic gene product is expressed at a very high level compared to that of the native gp120 controls. The molecular weight of the synthetic gp120 gene was comparable to control proteins (FIG. 3) and appeared to be in the range of 100 to 110 kd. The slightly faster migration can be explained by the fact that in some tumor cell lines like 293T glycosylation is either not complete or altered to some extent.

Figure 4:
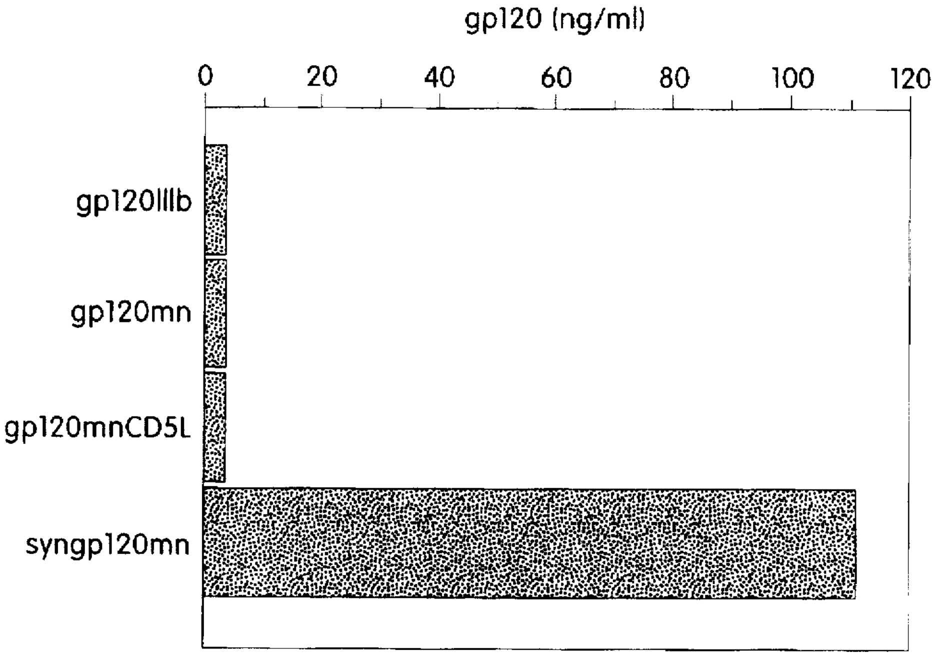
FIG. 4 is a graph depicting the results of ELISA assays used to measure protein levels in supernatants of transiently transfected 293T cells. Supernatants of 293T cells transfected with plasmids expressing gp120 encoded by the IIIB isolate of HIV-1 (gp120 IIIb), by the MN isolate (gp120mn), by the MN isolate modified by substitution of the endogenous leader peptide with that of CD5 antigen (gp120mn CD5L), or by the chemically synthesized gene encoding the MN variant with human CDS leader (syngp120mn) were harvested after 4 days and tested in a gp120/CD4 ELISA. The level of gp120 is expressed in ng/ml.

To compare expression more accurately gp120 protein levels were quantitated using a gp120 ELISA with CD4 in the demobilized phase. This analysis shows (FIG. 4) that ELISA data were comparable to the immunoprecipitation data, with a gp120 concentration of approximately 125 ng/ml for the synthetic gp120 gene, and less than the background cutoff (5 ng/ml) for all the native gp120 genes. Thus, expression of the synthetic gp120 gene appears to be at least one order of magnitude higher than wildtype gp120 genes. In the experiment shown the increase was at least 25 fold.

The Role of rev in gp120 Expression

Since rev appears to exert its effect at several steps in the expression of a viral transcript, the possible role of non-translational effects in the improved expression of the synthetic gp120 gene was tested. First, to rule out the possibility that negative signals elements conferring either increased mRNA degradation or nucleic retention were eliminated by changing the nucleotide sequence, cytoplasmic mRNA levels were tested. Cytoplasmic RNA was prepared by NP40 lysis of transiently transfected 293T cells and subsequent elimination of the nuclei by centrifugation. Cytoplasmic RNA was subsequently prepared from lysates by multiple phenol extractions and precipitation, spotted on nitrocellulose using a slot blot apparatus, and finally hybridized with an envelope-specific probe.

Briefly, cytoplasmic mRNA 293 cells transfected with CDM7, gp120IIIB, or syngp120 was isolated 36 hours post transfection. Cytoplasmic RNA of Hela cells infected with wildtype vaccinia virus or recombinant virus expressing gp120IIIb or the synthetic gp120 gene was under the control of the 7.5 promoter was isolated 16 hours post infection. Equal amounts were spotted on nitrocellulose using a slot blot device and hybridized with randomly labelled 1.5 kb gp120IIIb and syngp120 fragments or human beta-actin. RNA expression levels were quantitated by scanning the hybridized membranes with a phosphoimager. The procedures used are described in greater detail below.

This experiment demonstrated that there was no significant difference in the mRNA levels of cells transfected with either the native or synthetic gp120 gene. In fact, in some experiments cytoplasmic mRNA level of the synthetic gp120 gene was even lower than that of the native gp120 gene.

These data were confirmed by measuring expression from recombinant vaccinia viruses. Human 293 cells or Hela cells were infected with vaccinia virus expressing wildtype gp120IIIb or syngp120mn at a multiplicity of infection of at least 10. Supernatants were harvested 24 hours post infection and immunoprecipitated with CD4:immunoglobin fusion protein and protein A sepharose. The procedures used in this experiment are described in greater detail below.

This experiment showed that the increased expression of the synthetic gene was still observed when the endogenous gene product and the synthetic gene product were expressed from vaccinia virus recombinants under the control of the strong mixed early and late 7.5 k promoter. Because vaccinia virus mRNAs are transcribed and translated in the cytoplasm, increased expression of the synthetic envelope gene in this experiment cannot be attributed to improved export from the nucleus. This experiment was repeated in two additional human cell types, the kidney cancer cell line 293 and HeLa cells. As with transfected 293T cells, mRNA levels were similar in 293 cells infected with either recombinant vaccinia virus.

Codon Usage in Lentivirus

Because it appears that codon usage has a significant impact on expression in mammalian cells, the codon frequency in the envelope genes of other retroviruses was examined. This study found no clear pattern of codon preference between retroviruses in general. However, if viruses from the lentivirus genus, to which HIV-1 belongs were analyzed separately, codon usage bias almost identical to that of HIV-1 was found. A codon frequency table from the envelope glycoproteins of a variety of (predominantly type C) retroviruses excluding the lentiviruses was prepared, and a codon frequency table created from the envelope sequences of four lentiviruses not closely related to HIV-1 (caprine arthritis encephalitis virus, equine infectious anemia virus, feline immunodeficiency virus, and visna virus) (Table 2). The codon usage pattern for lentiviruses is strikingly similar to that of HIV-1. In all cases but one, the preferred codon for HIV-1 is the same as the preferred codon for the other lentiviruses. The exception is proline, which is encoded by CCT in 41% of non-HIV lentiviral envelope residues, and by CCA in 40% of residues, a situation which clearly also reflects a significant preference for the triplet ending in A. The pattern of codon usage by the non-lentiviral envelope proteins does not show a similar predominance of A residues, and is also not as skewed toward third position C and G residues as is the codon usage for the highly expressed human genes. In general non-lentiviral retroviruses appear to exploit the different codons more equally, a pattern they share with less highly expressed human genes.

TABLE 2

Codon frequency in the envelope gene of lentiviruses (lenti) and non-lentiviral retroviruses (other).

| | | Other | Lenti |
|---|---|---|---|
| Ala | | | |
| GC | C | 45 | 13 |
| | T | 26 | 37 |
| | A | 20 | 46 |
| | G | 9 | 3 |
| Arg | | | |
| CG | C | 14 | 2 |
| | T | 6 | 3 |
| | A | 16 | 5 |
| | G | 17 | 3 |
| AG | A | 31 | 51 |
| | G | 15 | 26 |
| Asn | | | |
| AA | C | 49 | 31 |
| | T | 51 | 69 |
| Asp | | | |
| GA | C | 55 | 33 |
| | T | 51 | 69 |
| Leu | | | |
| CT | C | 22 | 8 |
| | T | 14 | 9 |
| | A | 21 | 16 |
| | G | 19 | 11 |
| TT | A | 15 | 41 |
| | G | 10 | 16 |
| Lys | | | |
| AA | A | 60 | 63 |
| | G | 40 | 37 |
| Pro | | | |
| CC | C | 42 | 14 |
| | T | 30 | 41 |
| | A | 20 | 40 |
| | G | 7 | 5 |
| Phe | | | |
| TT | C | 52 | 25 |
| | T | 48 | 75 |
| Cys | | | |
| TG | C | 53 | 21 |
| | T | 47 | 79 |

TABLE 2-continued

Codon frequency in the envelope gene of lentiviruses (lenti) and non-lentiviral retroviruses (other).

| | | Other | Lenti |
|---|---|---|---|
| Gln | | | |
| CA | A | 52 | 69 |
| | C | 48 | 31 |
| Glu | | | |
| GA | A | 57 | 68 |
| | G | 43 | 32 |
| Gly | | | |
| CC | C | 21 | 8 |
| | T | 13 | 9 |
| | A | 37 | 56 |
| | G | 29 | 26 |
| His | | | |
| CA | C | 51 | 38 |
| | T | 49 | 62 |
| Ile | | | |
| AT | C | 38 | 16 |
| | T | 31 | 22 |
| | A | 31 | 61 |
| Ser | | | |
| TC | C | 38 | 10 |
| | T | 17 | 16 |
| | A | 18 | 24 |
| | G | 6 | 5 |
| AG | C | 13 | 20 |
| | T | 7 | 25 |
| Thr | | | |
| AC | C | 44 | 18 |
| | T | 27 | 20 |
| | A | 19 | 55 |
| | G | 10 | 8 |
| Tyr | | | |
| TA | C | 48 | 28 |
| | T | 52 | 72 |
| Val | | | |
| GT | C | 36 | 9 |
| | T | 17 | 10 |
| | A | 22 | 54 |
| | G | 25 | 27 |

Codon frequency was calculated using the GCG program established by the University of Wisconsin Genetics Computer Group. Numbers represent the percentage in which a particular codon is used. Codon usage of non-lentiviral retroviruses was compiled from the envelope precursor sequences of bovine leukemia virus feline leukemia virus, human T-cell leukemia virus type I, human T-cell lymphotropic virus type II, the mink cell focus-forming isolate of murine leukemia virus (MuLV), the Rauscher spleen focus-forming isolate, the 10A1 isolate, the 4070A amphotropic isolate and the myeloproliferative leukemia virus isolate, and from rat leukemia virus, simian sarcoma virus, simian T-cell leukemia virus, leukemogenic retrovirus T1223/B and gibbon ape leukemia virus. The codon frequency tables for the non-HIV, non-SIV lentiviruses were compiled from the envelope precursor sequences for caprine arthritis encephalitis virus, equine infectious anemia virus, feline immunodeficiency virus, and visna virus.

In addition to the prevalence of A containing codons, lentiviral codons adhere to the HIV pattern of strong CpG underrepresentation, so that the third position for alanine, proline, serine and threonine triplets is rarely G. The retroviral envelope triplets show a similar, but less pronounced, underrepresentation of CpG. The most obvious difference between lentiviruses and other retroviruses with respect to CpG prevalence lies in the usage of the CGX variant of arginine triplets, which is reasonably frequently represented among the retroviral envelope coding sequences, but is almost never present among the comparable lentivirus sequences.

Differences in rev Dependence Between Native and Synthetic gp120

To examine whether regulation by rev is connected to HIV-1 codon usage, the influence of rev on the expression of both native and synthetic gene was investigated. Since regulation by rev requires the rev-binding site RRE in cis, constructs were made in which this binding site was cloned into the 3' untranslated region of both the native and the synthetic gene. These plasmids were co-transfected with rev or a control plasmid in trans into 293T cells, and gp120 expression levels in supernatants were measured semiquantitatively by immunoprecipitation. The procedures used in this experiment are described in greater detail below.

Figure 5A:
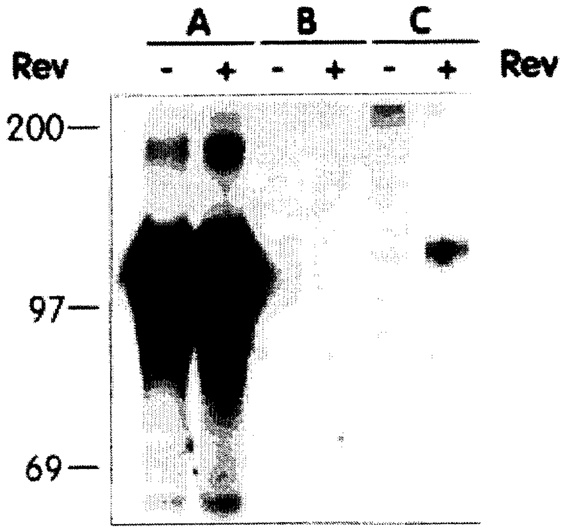
FIG. 5, panel A is a photograph of a gel illustrating the results of an immunoprecipitation assay used to measure expression of the native and synthetic gp120 in the presence of rev in trans and the RRE in cis. In this experiment 293T cells were transiently transfected by calcium phosphate coprecipitation of 10 μg of plasmid expressing: (A) the synthetic gp120MN sequence and RRE in cis, (B) the gp120 portion of HIV-1 IIIB, (C) the gp120 portion of HIV-1 IIIB and RRE in cis, all in the presence or absence of rev expression. The RRE constructs gp120IIIbRRE and syngp120mnRRE were generated using an Eag1/Hpa1 RRE fragment cloned by PCR from a HIV-1 HXB2 proviral clone. Each gp120 expression plasmid was cotransfected with 10 μg of either pCMVrev or CDM7 plasmid DNA. Supernatants were harvested 60 hours post transfection, immunoprecipitated with CD4:IgG fusion protein and protein A agarose, and run on a 7% reducing SDS-PAGE. The gel exposure time was extended to allow the induction of gp120IIIbrre by rev to be demonstrated.
Figure 5B:
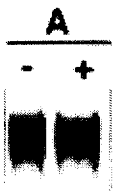
Figure 5C:
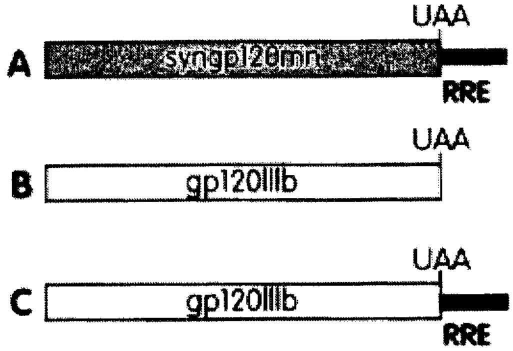

As shown in FIG. 5, panels A and B, rev upregulates the native gp120 gene, but has no effect on the expression of the synthetic gp120 gene. Thus, the action of rev is not apparent on a substrate which lacks the coding sequence of endogenous viral envelope sequences.

Expression of a synthetic rat THY-1 gene with HIV envelope codons

Figure 7:
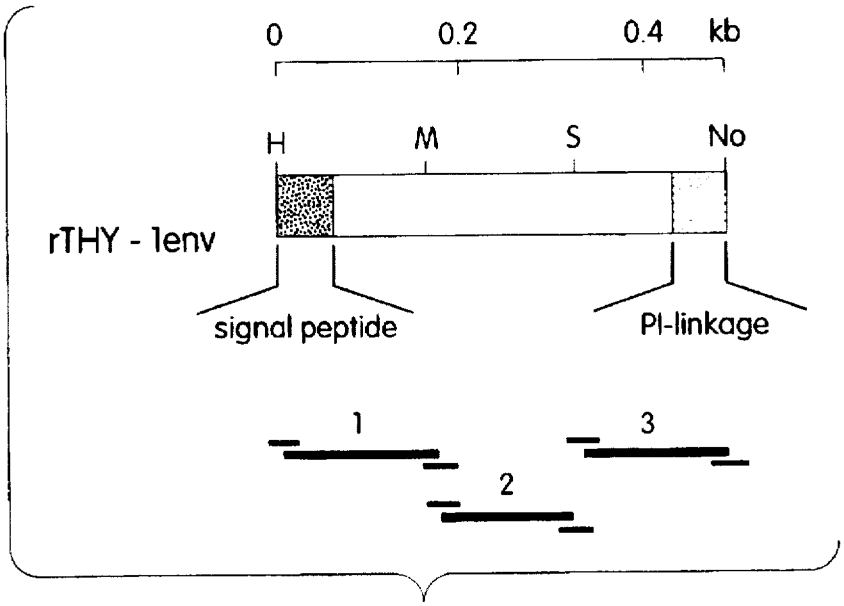
FIG. 7 is a schematic diagram of the synthetic ratTHY-1 gene. The solid black box denotes the signal peptide. The shaded box denotes the sequences in the precursor which direct the attachment of a phosphatidylinositol glycan anchor. Unique restriction sites used for assembly of the THY-1 constructs are marked H (Hind3), M (Mlu1), S (Sac1) and No (Not1). The position of the synthetic oligonucleotides employed in the construction are shown at the bottom of the figure.

The above-described experiment suggest that in fact "envelope sequences" have to be present for rev regulation. In order to test this hypothesis, a synthetic version of the gene encoding the small, typically highly expressed cell surface protein, rat THY-1 antigen, was prepared. The synthetic version of the rat THY-1 gene was designed to have a codon usage like that of HIV gp120. In designing this synthetic gene AUUUA sequences, which are associated with mRNA instability, were avoided. In addition, two restriction sites were introduced to simplify manipulation of the resulting gene (FIG. 6). This synthetic gene with the HIV envelope codon usage (rTHY-1env) was generated using three 150 to 170 mer oligonucleotides (FIG. 7). In contrast to the syngp120mn gene, PCR products were directly cloned and assembled in pUC12, and subsequently cloned into pCDM7.

Figure 8:
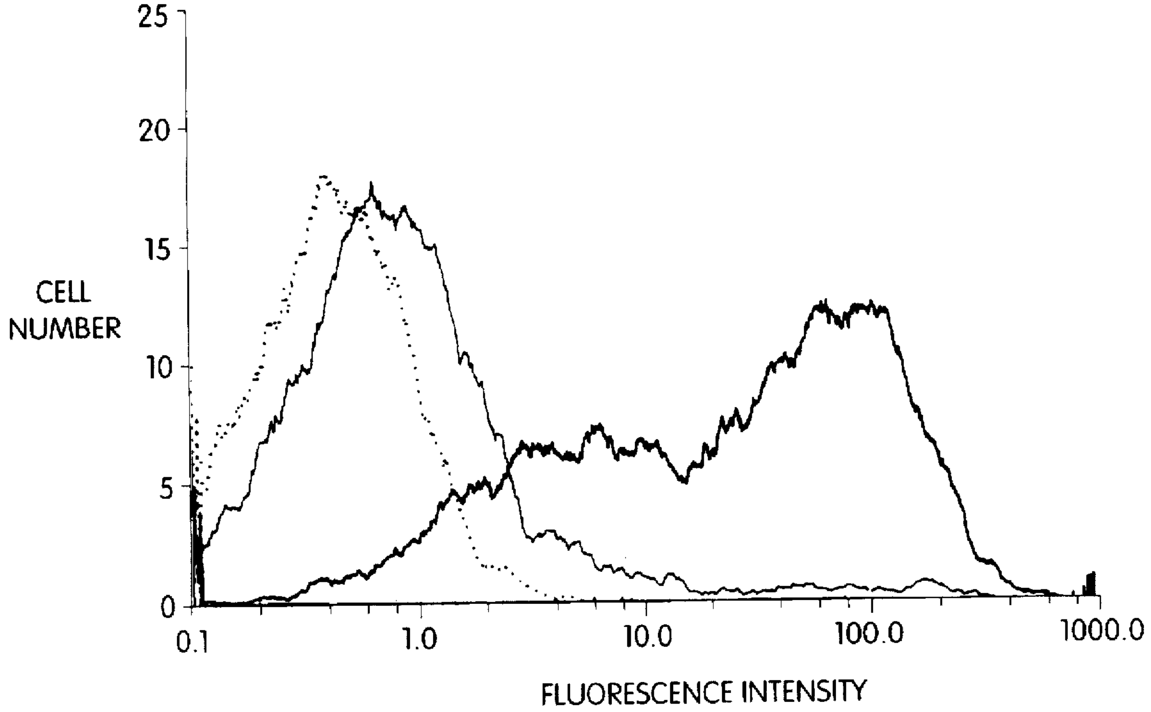
FIG. 8 is a graph depicting the results of flow cytometry analysis. In this experiment 293T cells were transiently transfected with either wildtype rat THY-1 (dark line), ratTHY-1 with envelope codons (light line) or vector only (dotted line). 293T cells were transfected with the different expression plasmids by calcium phosphate coprecipitation and stained with anti-ratTHY-1 monoclonal antibody OX7 followed by a polyclonal FITC- conjugated anti-mouse IgG antibody 3 days after transfection.

Expression levels of native rTHY-1 and rTHY-1 with the HIV envelope codons were quantitated by immunofluorescence of transiently transfected 293T cells. FIG. 8 shows that the expression of the native THY-1 gene is almost two orders of magnitude above the background level of the control transfected cells (pCDM7). In contrast, expression of the synthetic rat THY-1 is substantially lower than that of the native gene (shown by the shift of the peak towards a lower channel number).

Figure 9A:
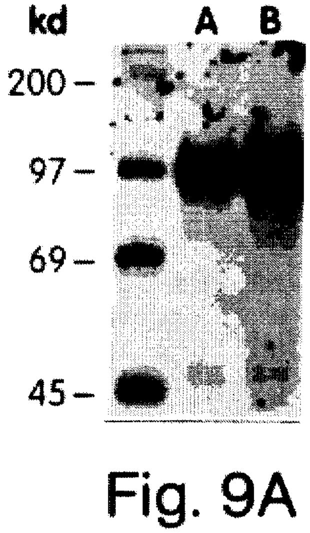
FIG. 9, panel A is a photograph of a gel illustrating the results of immunoprecipitation analysis of supernatants of human 293T cells transfected with either syngp120mn (lane A) or a construct syngp120mn.rTHY-1env which has the rTHY-1env gene in the 3' untranslated region of the syngp120mn gene (lane B). The syngp120mn.rTHY-1env construct was generated by inserting a Not1 adapter into the blunted Hind3 site of the rTHY-1env plasmid. Subsequently, a 0.5 kb Not1 fragment containing the rTHY-1env gene was cloned into the Not1 site of the syngp120mn plasmid and tested for correct orientation. Supernatants of 35 S labelled cells were harvested 72 hours post transfection, precipitated with CD4:IgG fusion protein and protein A agarose, and run on a 7% reducing SDS-PAGE.
Figure 9B:
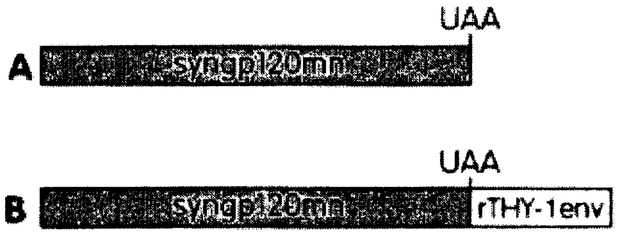

To prove that no negative sequence elements promoting mRNA degradation were inadvertently introduced, a construct was generated in which the rTHY-1env gene was cloned at the 3' end of the synthetic gp120 gene (FIG. 9, panel B). In this experiment 293T cells were transfected with either the syngp120mn gene or the syngp120/rat THY-1 env fusion gene (syngp120mn.rTHY-1env). Expression was measured by immunoprecipitation with CD4:IgG fusion protein and protein A agarose. The procedures used in this experiment are described in greater detail below.

Since the synthetic gp120 gene has a UAG stop codon, rTHY-1env is not translated from this transcript. If negative elements conferring enhanced degradation were present in the sequence, gp120 protein levels expressed from this construct should be decreased in comparison to the syngp120mn construct without rTHY-1env. FIG. 9, panel A, shows that the expression of both constructs is similar, indicating that the low expression must be linked to translation.

Rev-dependent expression of synthetic rat THY-1 gene with envelope codons

To explore whether rev is able to regulate expression of a rat THY-1 gene having env codons, a construct was made with a rev-binding site in the 3' end of the rTHY1env open reading frame. To measure rev-responsiveness of the a rat THY-1env construct having a 3' RRE, human 293T cells were cotransfected with ratTHY-1envrre and either CDM7 or pCMVrev. At 60 hours post transfection cells were detached with 1 mM EDTA in PBS and stained with the OX-7 anti rTHY-1 mouse monoclonal antibody and a secondary FITC-conjugated antibody. Fluorescence intensity was measured using an EPICS XL cytofluorometer. These procedures are described in greater detail below.

In repeated experiments, a slight increase of rTHY-1env expression was detected if rev was cotransfected with the rTHY-1env gene. To further increase the sensitivity of the assay system a construct expressing a secreted version of rTHY-1env was generated. This construct should produce more reliable data because the accumulated amount of secreted protein in the supernatant reflects the result of protein production over an extended period, in contrast to surface expressed protein, which appears to more closely reflect the current production rate. A gene capable of expressing a secreted form was prepared by PCR using forward and reverse primers annealing 3' of the endogenous leader sequence and 5' of the sequence motif required for phosphatidylinositol glycan anchorage respectively. The PCR product was cloned into a plasmid which already contained a CD5 leader sequence, thus generating a construct in which the membrane anchor has been deleted and the leader sequence exchanged by a heterologous (and probably more efficient) leader peptide.

The rev-responsiveness of the secreted form ratTHY-1env was measured by immunoprecipitation of supernatants of human 293T cells cotransfected with a plasmid expressing a secreted form of ratTHY-1env and the RRE sequence in cis (rTHY-1envPI-rre) and either CDM7 or pCMVrev. The rTHY-1envPI-RRE construct was made by PCR using the oligonucleotides cgcggggctagcgcaaagagtaataagtttaac as forward and cgcggatcccttgtattttgtactaata a as reverse primers and the synthetic rTHY-1env construct as template. After digestion with Nhe1 and Not1 the PCR fragment was cloned into a plasmid containing CD5 leader and RRE sequences. Supernatants of $^{35}S$ labelled cells were harvested 72 hours post transfection, precipitated with a mouse monoclonal antibody OX7 against rTHY-1 and anti-mouse IgG sepharose, and run on a 12% reducing SDS-PAGE.

In this experiment the induction of rTHY-1env by rev was much more prominent and clearcut than in the above-described experiment and strongly suggests that rev is able to translationally regulate transcripts that are suppressed by low-usage codons.

Rev-independent expression of a rTHY-1env:immunoglobulin fusion protein

To test whether low-usage codons must be present throughout the whole coding sequence or whether a short region is sufficient to confer rev-responsiveness, a rTHY-1env:immunoglobulin fusion protein was generated. In this construct the rTHY-1env gene (without the sequence motif responsible for phosphatidylinositol glycan anchorage) is linked to the human IgG1 hinge, CH2 and CH3 domains. This construct was generated by anchor PCR using primers with Nhe1 and BamHI restriction sites and rTHY-1env as template. The PCR fragment was cloned into a plasmid containing the leader sequence of the CD5 surface molecule and the hinge, CH2 and CH3 parts of human IgG1 immu noglobulin. A Hind3/Eag1 fragment containing the rTHY-1enveg1 insert was subsequently cloned into a pCDM7-derived plasmid with the RRE sequence.

To measure the response of the rTHY-1env/immunoglobin fusion gene (rTHY-1enveg1rre) to rev human 293T cells cotransfected with rTHY-1enveg1rre and either pCDM7 or pCMVrev. The rTHY-1enveg1rre construct was made by anchor PCR using forward and reverse primers with Nhe1 and BamH1 restriction sites respectively. The PCR fragment was cloned into a plasmid containing a CD5 leader and human IgG1 hinge, CH2 and CH3 domains. Supernatants of $^{35}S$ labelled cells were harvested 72 hours post transfection, precipitated with a mouse monoclonal antibody OX7 against rTHY-1 and anti mouse IgG sepharose, and run on a 12% reducing SDS-PAGE. The procedures used are described in greater detail below.

As with the product of the rTHY-1envPI-gene, this rTHY-1env/immunoglobulin fusion protein is secreted into the supernatant. Thus, this gene should be responsive to rev-induction. However, in contrast to rTHY-1envPI-, cotransfection of rev in trans induced no or only a negligible increase of rTHY-1enveg1 expression.

The expression of rTHY-1:immunoglobulin fusion protein with native rTHY-1 or HIV envelope codons was measured by immunoprecipitation. Briefly, human 293T cells transfected with either rTHY-1enveg1 (env codons) or rTHY-1wteg1 (native codons). The rTHY-1wteg1 construct was generated in manner similar to that used for the rTHY-1enveg1 construct, with the exception that a plasmid containing the native rTHY-1 gene was used as template. Supernatants of $^{35}S$ labelled cells were harvested 72 hours post transfection, precipitated with a mouse monoclonal antibody OX7 against rTHY-1 and anti mouse IgG sepharose, and run on a 12% reducing SDS-PAGE. The procedures used in this experiment are described in greater detail below.

Expression levels of rTHY-1enveg1 were decreased in comparison to a similar construct with wildtype rTHY-1 as the fusion partner, but were still considerably higher than rTHY-1env. Accordingly, both parts of the fusion protein influenced expression levels. The addition of rTHY-1env did not restrict expression to an equal level as seen for rTHY-1env alone. Thus, regulation by rev appears to be ineffective if protein expression is not almost completely suppressed.

Codon preference in HIV-1 envelope genes

Direct comparison between codon usage frequency of HIV envelope and highly expressed human genes reveals a striking difference for all twenty amino acids. One simple measure of the statistical significance of this codon preference is the finding that among the nine amino acids with two fold codon degeneracy, the favored third residue is A or U in all nine. The probability that all nine of two equiprobable choices will be the same is approximately 0.004, and hence by any conventional measure the third residue choice cannot be considered random. Further evidence of a skewed codon preference is found among the more degenerate codons, where a strong selection for triplets bearing adenine can be seen. This contrasts with the pattern for highly expressed genes, which favor codons bearing C, or less commonly G, in the third position of codons with three or more fold degeneracy.

The systematic exchange of native codons with codons of highly expressed human genes dramatically increased expression of gp120. A quantitative analysis by ELISA showed that expression of the synthetic gene was at least 25 fold higher in comparison to native gp120 after transient transfection into human 293 cells. The concentration levels in the ELISA experiment shown were rather low. Since an ELISA was used for quantification which is based on gp120 binding to CD4, only native, non-denatured material was detected. This may explain the apparent low expression. Measurement of cytoplasmic mRNA levels demonstrated that the difference in protein expression is due to translational differences and not mRNA stability.

Retroviruses in general do not show a similar preference towards A and T as found for HIV. But if this family was divided into two subgroups, lentiviruses and non-lentiviral retroviruses, a similar preference to A and, less frequently, T, was detected at the third codon position for lentiviruses. Thus, the availing evidence suggests that lentiviruses retain a characteristic pattern of envelope codons not because of an inherent advantage to the reverse transcription or replication of such residues, but rather for some reason peculiar to the physiology of that class of viruses. The major difference between lentiviruses and non-complex retroviruses are additional regulatory and non-essentially accessory genes in lentiviruses, as already mentioned. Thus, one simple explanation for the restriction of envelope expression might be that an important regulatory mechanism of one of these additional molecules is based on it. In fact, it is known that one of these proteins, rev, which most likely has homologues in all lentiviruses. Thus codon usage in viral mRNA is used to create a class of transcripts which is susceptible to the stimulatory action of rev. This hypothesis was proved using a similar strategy as above, but this time codon usage was changed into the inverse direction. Codon usage of a highly expressed cellular gene was substituted with the most frequently used codons in the HIV envelope. As assumed, expression levels were considerably lower in comparison to the native molecule, almost two orders of magnitude when analyzed by immunofluorescence of the surface expressed molecule (see 4.7). If rev was coexpressed in trans and an RRE element was present in cis only a slight induction was found for the surface molecule. However, if THY-1 was expressed as a secreted molecule, the induction by rev was much more prominent, supporting the above hypothesis. This can probably be explained by accumulation of secreted protein in the supernatant, which considerably amplifies the rev effect. If rev only induces a minor increase for surface molecules in general, induction of HIV envelope by rev cannot have the purpose of an increased surface abundance, but rather of an increased intracellular gp160 level. It is completely unclear at the moment why this should be the case.

To test whether small subtotal elements of a gene are sufficient to restrict expression and render it rev-dependent rTHY1env:immunoglobulin fusion proteins were generated, in which only about one third of the total gene had the envelope codon usage. Expression levels of this construct were on an intermediate level, indicating that the rTHY-1env negative sequence element is not dominant over the immunoglobulin part. This fusion protein was not or only slightly rev-responsive, indicating that only genes almost completely suppressed can be rev-responsive.

Another characteristic feature that was found in the codon frequency tables is a striking underrepresentation of CpG triplets. In a comparative study of codon usage in *E. coli*, yeast, drosophila and primates it was shown that in a high number of analyzed primate genes the 8 least used codons contain all codons with the CpG dinucleotide sequence. Avoidance of codons containing this dinucleotide motif was also found in the sequence of other retroviruses. It seems plausible that the reason for underrepresentation of CpG-bearing triplets has something to do with avoidance of gene silencing by methylation of CpG cytosines. The expected number of CpG dinucleotides for HIV as a whole is about one fifth that expected on the basis of the base composition. This might indicate that the possibility of high expression is restored, and that the gene in fact has to be highly expressed at some point during viral pathogenesis.

The results presented herein clearly indicate that codon preference has a severe effect on protein levels, and suggest that translational elongation is controlling mammalian gene expression. However, other factors may play a role. First, abundance of not maximally loaded mRNA's in eukaryotic cells indicates that initiation is rate limiting for translation in at least some cases, since otherwise all transcripts would be completely covered by ribosomes. Furthermore, if ribosome stalling and subsequent mRNA degradation were the mechanism, suppression by rare codons could most likely not be reversed by any regulatory mechanism like the one presented herein. One possible explanation for the influence of both initiation and elongation on translational activity is that the rate of initiation, or access to ribosomes, is controlled in part by cues distributed throughout the RNA, such that the lentiviral codons predispose the RNA to accumulate in a pool of poorly initiated RNAs. However, this limitation need not be kinetic; for example, the choice of codons could influence the probability that a given translation product, once initiated, is properly completed. Under this mechanism, abundance of less favored codons would incur a significant cumulative probability of failure to complete the nascent polypeptide chain. The sequestered RNA would then be lent an improved rate of initiation by the action of rev. Since adenine residues are abundant in rev-responsive transcripts, it could be that RNA adenine methylation mediates this translational suppression.

Detailed Procedures

The following procedures were used in the above-described experiments.

Sequence Analysis

Sequence analyses employed the software developed by the University of Wisconsin Computer Group.

Plasmid constructions

Plasmid constructions employed the following methods. Vectors and insert DNA was digested at a concentration of 0.5 μg/10 μl in the appropriate restriction buffer for 1–4 hours (total reaction volume approximately 30 μl). Digested vector was treated with 10% (v/v) of 1 μg/ml calf intestine alkaline phosphatase for 30 min prior to gel electrophoresis. Both vector and insert digests (5 to 10 μl each) were run on a 1.5% low melting agarose gel with TAE buffer. Gel slices containing bands of interest were transferred into a 1.5 ml reaction tube, melted at 65° C. and directly added to the ligation without removal of the agarose. Ligations were typically done in a total volume of 25 μl in 1× Low Buffer 1× Ligation Additions with 200–400 U of ligase, 1 μl of vector, and 4 μl of insert. When necessary, 5' overhanging ends were filled by adding 1/10 volume of 250 μM dNTPs and 2–5 U of Klenow polymerase to heat inactivated or phenol extracted digests and incubating for approximately 20 min at room temperature. When necessary, 3' overhanging ends were filled by adding 1/10 volume of 2.5 mM dNTPs and 5–10 U of T4 DNA polymerase to heat inactivated or phenol extracted digests, followed by incubation at 37° C. for 30 min. The following buffers were used in these reactions: 10× Low buffer (60 mM Tris HCl, pH 7.5, 60 mM $MgCl_2$, 50 mM NaCl, 4 mg/ml BSA, 70 mM β-mercaptoethanol, 0.02% $NaN_3$); 10× Medium buffer (60 mM Tris HCl, pH 7.5, 60 mM $MgCl_2$, 50 mM NaCl, 4 mg/ml BSA, 70 mM β-mercaptoethanol, 0.02% $NaN_3$); 10× High buffer (60 mM Tris HCl, pH 7.5, 60 mM $MgCl_2$, 50 mM NaCl, 4 mg/ml BSA, 70 mM β-mercaptoethanol, 0.02% $NaN_3$); 10× Ligation additions (1 mM ATP, 20 mM DTT, 1 mg/ml BSA, 10 mM spermidine); 50× TAE (2M Tris acetate, 50 mM EDTA).

Oligonucleotide synthesis and purification

Oligonucleotides were produced on a Milligen 8750 synthesizer (Millipore). The columns were eluted with 1 ml of 30% ammonium hydroxide, and the eluted oligonucleotides were deblocked at 55° C. for 6 to 12 hours. After deblockiong, 150 μl of oligonucleotide were precipitated with 10× volume of unsaturated n-butanol in 1.5 ml reaction tubes, followed by centrifugation at 15,000 rpm in a microfuge. The pellet was washed with 70% ethanol and resuspended in 50 μl of $H_2O$. The concentration was determined by measuring the optical density at 260 nm in a dilution of 1:333 (1 $OD_{260}$=30 μg/ml).

The following oligonucleotides were used for construction of the synthetic gp120 gene (all sequences shown in this text are in 5' to 3' direction).

oligo 1 forward (Nhe1): cgc ggg cta gcc acc gag aag ctg (SEQ ID NO:1).

oligo 1: acc gag aag ctg tgg gtg acc gtg tac tac ggc gtg ccc gtg tgg aag ag ag gcc acc acc acc ctg ttc tgc gcc agc gac gcc aag gcg tac gac acc gag gtg cac aac gtg tgg gcc acc cag gcg tgc gtg ccc acc gac ccc aac ccc cag gag gtg gag ctc gtg aacgtg acc gag aac ttc aac atg (SEQ ID NO:2).

oligo 1 reverse: cca cca tgt tgt tct tcc aca tgt tga agt tct c (SEQ ID NO:3).

oligo 2 forward: gac cga gaa ctt caa cat gtg gaa gaa caa cat (SEQ ID NO:4)

oligo 2: tgg aag aac aac atg gtg gag cag atg cat gag gac atc atc agc ctg tgg gac cag agc ctg aag ccc tgc gtg aag ctg acc cc ctg tgc gtg acc tg aac tgc acc gac ctg agg aac acc acc aac acc aac ac agc acc gcc aac aac aac agc aac agc gag ggc acc atc aag ggc ggc gag atg (SEQ ID NO:5).

oligo 2 reverse (Pst1): gtt gaa gct gca gtt ctt cat ctc gcc gcc ctt (SEQ ID NO:6).

oligo 3 forward (Pst1): gaa gaa ctg cag ctt caa cat cac cac cag c (SEQ ID NO:7).

oligo 3: aac atc acc acc agc atc cgc gac aag atg cag aag gag tac gcc ctg ctg tac aag ctg gat atc gtg agc atc gac aac gac agc acc agc tac cgc ctg atc tcc tgc aac acc agc gtg atc acc cag gcc tgc ccc aag atc agc ttc gag ccc atc ccc atc cac tac tgc gcc ccc gcc ggc ttc gcc (SEQ ID NO:8).

oligo 3 reverse: gaa ctt ctt gtc ggc ggc gaa gcc ggc ggg (SEQ ID NO:9).

oligo 4 forward: gcg ccc ccg ccg gct tcg cca tcc tga agt gca acg aca aga agt tc (SEQ ID NO:10)

oligo 4: gcc gac aag aag ttc agc ggc aag ggc agc tgc aag aac gtg agc acc gtg cag tgc acc cac ggc atc cgg ccg gtg gtg agc acc cag ctc ctg ctg aac ggc agc ctg gcc gag gag gag gtg gtg atc cgc agc gag aac ttc acc gac aac gcc aag acc atc atc gtg cac ctg aat gag agc gtg cag atc (SEQ ID NO:11)

oligo 4 reverse (Mlu1): agt tgg gac gcg tgc agt tga tct gca cgc tct c (SEQ ID NO:12).

oligo 5 forward (Mlu1): gag agc gtg cag atc aac tgc acg cgt ccc (SEQ ID NO:13).

oligo 5: aac tgc acg cgt ccc aac tac aac aag cgc aag cgc atc cac atc ggc ccc ggg cgc gcc ttc tac acc acc aag aac atc atc ggc acc atc ctc cag gcc cac tgc aac atc tct aga (SEQ ID NO:14).

oligo 5 reverse: gtc gtt cca ctt ggc tct aga gat gtt gca (SEQ ID NO:15).

oligo 6 forward: gca aca tct cta gag cca agt gga acg ac (SEQ ID NO:16).

oligo 6: gcc aag tgg aac gac acc ctg cgc cag atc gtg agc aag ctg aag gag cag ttc aag aac aag acc atc gtg ttc ac cag agc agc ggc ggc gac ccc gag atc gtg atg cac agc ttc aac tgc ggc ggc (SEQ ID NO:17).

oligo 6 reverse (EcoR1): gca gta gaa gaa ttc gcc gcc gca gtt ga (SEQ ID NO:18).

oligo 7 forward (EcoR1): tca act gcg gcg gcg aat tct tct act gc (SEQ ID NO:19).

oligo 7: ggc gaa ttc ttc tac tgc aac acc agc ccc ctg ttc aac agc acc tgg aac ggc aac aac acc tgg aac aac acc acc ggc agc aac aac aat att acc ctc cag tgc aag atc aag cag atc atc aac atg tgg cag gag gtg ggc aag gcc atg tac gcc ccc ccc atc gag ggc cag atc cgg tgc agc agc (SEQ ID NO:20)

oligo 7 reverse: gca gac cgg tga tgt tgc tgc tgc acc gga tct ggc cct c (SEQ ID NO:21).

oligo 8 forward: cga ggg cca gat ccg gtg cag cag caa cat cac cgg tct g (SEQ ID NO:22).

oligo 8: aac atc acc ggt ctg ctg ctg acc cgc gac ggc ggc aag gac acc gac acc aac gac acc gaa atc ttc cgc ccc ggc ggc ggc gac atg cgc gac aac tgg aga tct gag ctg tac aag tac aag gtg gtg acg atc gag ccc ctg ggc gtg gcc ccc acc aag gcc aag cgc cgc gtg gtg cag cgc gag aag cgc (SEQ ID NO:23).

oligo 8 reverse (Not1): cgc ggg cgg ccg ctt tag cgc ttc tcg cgc tgc acc ac (SEQ ID NO:24).

The following oligonucleotides were used for the construction of the ratTHY-1env gene.

oligo 1 forward (BamH1/Hind3): cgc ggg gga tcc aag ctt acc atg att cca gta ata agt (SEQ ID NO:25).

oligo 1: atg aat cca gta ata agt ata aca tta tta tta agt gta tta caa atg agt aga gga caa aga gta ata agt tta aca gca tct tta gta aat caa aat ttg aga tta gat tgt aga cat gaa aat aat aca aat ttg cca ata caa cat gaa ttt tca tta acg (SEQ ID NO:26).

oligo 1 reverse (EcoR1/Mlu1): cgc ggg gaa ttc acg cgt taa tga aaa ttc atg ttg (SEQ ID NO:27).

oligo 2 forward (BamH1/Mlu1): cgc gga tcc acg cgt gaa aaa aaa aaa cat (SEQ ID NO:28).

oligo 2: cgt gaa aaa aaa aaa cat gta tta agt gga aca tta gga gta cca gaa cat aca tat aga agt aga gta aat ttg ttt agt gat aga ttc ata aaa gta tta aca tta gca aat ttt aca aca aaa gat gaa gga gat tat atg tgt gag (SEQ ID NO:29).

oligo 2 reverse (EcoR1/Sac1): cgc gaa ttc gag ctc aca cat ata atc tcc (SEQ ID NO:30).

oligo 3 forward (BamH1/Sac1): cgc gga tcc gag ctc aga gta agt gga caa (SEQ ID NO:31).

oligo 3: ctc aga gta agt gga caa aat cca aca agt agt aat aaa aca ata aat gta ata aga gat aaa tta gta aaa tgt ga gga ata agt tta tta gta caa aat aca agt tgg tta tta tta tta tta tta agt tta agt ttt tta caa gca aca gat ttt ata agt tta tga (SEQ ID NO:32).

oligo 3 reverse (EcoR1/Not1): cgc gaa ttc gcg gcc gct tca taa act tat aaa atc (SEQ ID NO:33).

Polymerase Chain Reaction

Short, overlapping 15 to 25 mer oligonucleotides annealing at both ends were used to amplify the long oligonuclotides by polymerase chain reaction (PCR). Typical PCR conditions were: 35 cycles, 55° C. annealing temperature, 0.2 sec extension time. PCR products were gel purified, phenol extracted, and used in a subsequent PCR to generate longer fragments consisting of two adjacent small fragments. These longer fragments were cloned into a CDM7-derived plasmid containing a leader sequence of the CD5 surface molecule followed by a Nhe1/Pst1/Mlu1/EcoR1/BamH1 polylinker.

The following solutions were used in these reactions: 10× PCR buffer (500 mM KCl, 100 mM Tris HCl, pH 7.5, 8 mM $MgCl_2$, 2 mM each dNTP). The final buffer was complemented with 10% DMSO to increase fidelity of the Taq polymerase.

Small scale DNA preparation

Transformed bacteria were grown in 3 ml LB cultures for more than 6 hours or overnight. Approximately 1.5 ml of each culture was poured into 1.5 ml microfuge tubes, spun for 20 seconds to pellet cells and resuspended in 200 μl of solution I. Subsequently 400 μl of solution II and 300 μl of solution III were added. The microfuge tubes were capped, mixed and spun for >30 sec. Supernatants were transferred into fresh tubes and phenol extracted once. DNA was precipitated by filling the tubes with isopropanol, mixing, and spinning in a microfuge for >2 min. The pellets were rinsed in 70 % ethanol and resuspended in 50 μl $dH_2O$ containing 10 μl of RNAse A. The following media and solutions were used in these procedures: LB medium (1.0% NaCl, 0.5% yeast extract, 1.0% trypton); solution I (10 mM EDTA pH 8.0); solution II (0.2M NaOH, 1.0% SDS); solution III (2.5M KOAc, 2.5M glacial aceatic acid); phenol (pH adjusted to 6.0, overlaid with TE); TE (10 mM Tris HCl, pH 7.5, 1 mM EDTA pH 8.0).

Large scale DNA preparation

One liter cultures of transformed bacteria were grown 24 to 36 hours (MC1061p3 transformed with pCDM derivatives) or 12 to 16 hours (MC1061 transformed with pUC derivatives) at 37° C. in either M9 bacterial medium (pCDM derivatives) or LB (pUC derivatives). Bacteria were spun down in 1 liter bottles using a Beckman J6 centrifuge at 4,200 rpm for 20 min. The pellet was resuspended in 40 ml of solution I. Subsequently, 80 ml of solution II and 40 ml of solution III were added and the bottles were shaken semivigorously until lumps of 2 to 3 mm size developed. The bottle was spun at 4,200 rpm for 5 min and the supernatant was poured through cheesecloth into a 250 ml bottle. Isopropanol was added to the top and the bottle was spun at 4,200 rpm for 10 min. The pellet was resuspended in 4.1 ml of solution I and added to 4.5 g of cesium chloride, 0.3 ml of 10 mg/ml ethidium bromide, and 0.1 ml of 1% Triton X100 solution. The tubes were spun in a Beckman J2 high speed centrifuge at 10,000 rpm for 5 min. The supernatant was transferred into Beckman Quick Seal ultracentrifuge tubes, which were then sealed and spun in a Beckman ultracentrifuge using a NVT90 fixed angle rotor at 80,000 rpm for >2.5 hours. The band was extracted by visible light using a 1 ml syringe and 20 gauge needle. An equal volume of $dH_2O$ was added to the extracted material. DNA was extracted once with n-butanol saturated with 1M sodium chloride, followed by addition of an equal volume of 10M ammonium acetate/1 mM EDTA. The material was poured into a 13 ml snap tube which was than filled to the top with absolute ethanol, mixed, and spun in a Beckman J2 centrifuge at 10,000 rpm for 10 min. The pellet was rinsed with 70% ethanol and resuspended in 0.5 to 1 ml of $H_2O$. The DNA concentration was determined by measuring the optical density at 260 nm in a dilution of 1:200 (1 $OD_{260}$=50 μg/ml).

The following media and buffers were used in these procedures: M9 bacterial medium (10 g M9 salts, 10 g casamino acids (hydrolysed), 10 ml M9 additions, 7.5 µg/ml tetracycline (500 µl of a 15 mg/ml stock solution), 12.5 µg/ml ampicillin (125 µl of a 10 mg/ml stock solution); M9 additions (10 mM $CaCl_2$, 100 mM $MgSO_4$, 200 µg/ml thiamine, 70% glycerol); LB medium (1.0% NaCl, 0.5% yeast extract, 1.0% trypton); Solution I (10 mM EDTA pH 8.0); Solution II (0.2M NaOH 1.0% SDS); Solution III (2.5M KOAC 2.5M HOAc)

Sequencing

Synthetic genes were sequenced by the Sanger dideoxy-nucleotide method. In brief, 20 to 50 µg double-stranded plasmid DNA were denatured in 0.5M NaOH for 5 min. Subsequently the DNA was precipitated with 1/10 volume of sodium acetate (pH 5.2) and 2 volumes of ethanol and centrifuged for 5 min. The pellet was washed with 70% ethanol and resuspended at a concentration of 1 µg/µl. The annealing reaction was carried out with 4 µg of template DNA and 40 ng of primer in 1× annealing buffer in a final volume of 10 µl. The reaction was heated to 65° C. and slowly cooled to 37° C. In a separate tube 1 µl of 0.1M DTT, 2 µl of labeling mix, 0.75 µl of $dH_2O$, 1 µl of [$^{35}S$] dATP (10 µCi), and 0.25 µl of Sequenase™ (12 U/µl) were added for each reaction. Five µl of this mix were added to each annealed primer-template tube and incubated for 5 min at room temperature. For each labeling reaction 2.5 µl of each of the 4 termination mixes were added on a Terasaki plate and prewarmed at 37° C. At the end of the incubation period 3.5 µl of labeling reaction were added to each of the 4 termination mixes. After 5 min, 4 µl of stop solution were added to each reaction and the Terasaki plate was incubated at 80° C. for 10 min in an oven. The sequencing reactions were run on 5% denaturing polyacrylamide gel. An acrylamide solution was prepared by adding 200 ml of 10× TBE buffer and 957 ml of $dH_2O$ to 100 g of acrylamide:bisacrylamide (29:1). 5% polyacrylamide 46% urea and 1×TBE gel was prepared by combining 38 ml of acrylamide solution and 28 g urea. Polymerization was initiated by the addition of 400 µl of 10% ammonium peroxodisulfate and 60 µl of TEMED. Gels were poured using silanized glass plates and sharktooth combs and run in 1× TBE buffer at 60 to 100 W for 2 to 4 hours (depending on the region to be read). Gels were transferred to Whatman blotting paper, dried at 80° C. for about 1 hour, and exposed to x-ray film at room temperature. Typically exposure time was 12 hours. The following solutions were used in these procedures: 5× Annealing buffer (200 mM Tris HCl, pH 7.5, 100 mM $MgCl_2$, 250 mM NaCl); Labelling Mix (7.5 µM each dCTP, dGTP, and dTTP); Termination Mixes (80 µM each dNTP, 50 mM NaCl, 8 µM ddNTP (one each)); Stop solution (95% formamide, 20 mM EDTA, 0.05% bromphenol blue, 0.05% xylencyanol); 5× TBE (0.9M Tris borate, 20 mM EDTA); Polyacrylamide solution (96.7 g polyacrylamide, 3.3 g bisacrylamide, 200 ml 1× TBE, 957 ml $dH_2O$).

RNA isolation

Cytoplasmic RNA was isolated from calcium phosphate transfected 293T cells 36 hours post transfection and from vaccinia infected Hela cells 16 hours post infection essentially as described by Gilman. (Gilman Preparation of cytoplasmic RNA from tissue culture cells. In *Current Protocols in Molecular Biology*, Ausubel et al, eds., Wiley & Sons, New York, 1992). Briefly, cells were lysed in 400 µl lysis buffer, nuclei were spun out, and SDS and proteinase K were added to 0.2% and 0.2 mg/ml respectively. The cytoplasmic extracts were incubated at 37° C. for 20 min, phenol/chloroform extracted twice, and precipitated. The RNA was dissolved in 100 µl buffer I and incubated at 37° C. for 20 min. The reaction was stopped by adding 25 µl stop buffer and precipitated again.

The following solutions were used in this procedure: Lysis Buffer (TE containing with 50 mM Tris pH 8.0, 100 mM NaCl, 5 mM $MgCl_2$, 0.5% NP40); Buffer I (TE buffer with 10 mM $MgCl_2$, 1 mM DTT, 0.5 U/µl placental RNAse inhibitor, 0.1 U/µl RNAse free DNAse I); Stop buffer (50 mM EDTA 1.5M NaOAc 1.0% SDS).

Slot blot analysis

For slot blot analysis 10 µg of cytoplasmic RNA was dissolved in 50 µl $dH_2O$ to which 150 µl of 10× SSC/18% formaldehyde were added. The solubilized RNA was then incubated at 65° C. for 15 min and spotted onto with a slot blot apparatus. Radioactively labelled probes of 1.5 kb gp120IIIb and syngp120mn fragments were used for hybridization. Each of the two fragments was random labelled in a 50 µl reaction with 10 µl of 5× oligo-labelling buffer, 8 µl of 2.5 mg/ml BSA, 4 µl of α[$^{32}P$]-dCTP (20 uCi/µl; 6000 Ci/mmol), and 5 U of Klenow fragment. After 1 to 3 hours incubation at 37° C. 100 µl of TE were added and unincorporated α[$^{32}P$]-dCTP was eliminated using a G50 spin column. Activity was measured in a Beckman beta-counter, and equal specific activities were used for hybridization. Membranes were pre-hybridized for 2 hours and hybridized for 12 to 24 hours at 42° C. with $0.5\times10^6$ cpm probe per ml hybridization fluid. The membrane was washed twice (5 min) with washing buffer I at room temperature, for one hour in washing buffer II at 65° C., and then exposed to x-ray film. Similar results were obtained using a 1.1 kb Notl/SfiI fragment of pCDM7 containing the 3' untranslated region. Control hybridizations were done in parallel with a random-labelled human beta-actin probe. RNA expression was quantitated by scanning the hybridized nitrocellulose membranes with a Magnetic Dynamics phosphorimager.

The following solutions were used in this procedure: 5× Oligo-labelling buffer (250 mM Tris HCl, pH 8.0, 25 mM $MgCl_2$, 5 mM β-mercaptoethanol, 2 mM dATP, 2 mM dGTP, 2 mM dTTP, 1M Hepes pH 6.6, 1 mg/ml hexanucleotides [dNTP]6); Hybridization Solution (_M sodium phosphate, 250 mM NaCl, 7% SDS, 1 mM EDTA, 5% dextrane sulfate, 50% formamide, 100 µg/ml denatured salmon sperm DNA); Washing buffer I (2× SSC, 0.1% SDS); Washing buffer II (0.5× SSC, 0.1% SDS); 20× SSC (3M NaCl, 0.3M $Na_3$citrate, pH adjusted to 7.0).

Vaccinia recombination

Vaccinia recombination used a modification of the method described by Romeo and Seed (Romeo and Seed, *Cell*, 64: 1037, 1991). Briefly, CV1 cells at 70 to 90% confluency were infected with 1 to 3 µl of a wildtype vaccinia stock WR ($2\times10^8$ pfu/ml) for 1 hour in culture medium without calf serum. After 24 hours, the cells were transfected by calcium phosphate with 25 µg TKG plasmid DNA per dish. After an additional 24 to 48 hours the cells were scraped off the plate, spun down, and resuspended in a volume of 1 ml. After 3 freeze/thaw cycles trypsin was added to 0.05 mg/ml and lysates were incubated for 20 min. A dilution series of 10, 1 and 0.1 µl of this lysate was used to infect small dishes (6 cm) of CV1 cells, that had been pretreated with 12.5 µg/ml mycophenolic acid, 0.25 mg/ml xanthin and 1.36 mg/ml hypoxanthine for 6 hours. Infected cells were cultured for 2 to 3 days, and subsequently stained with the monoclonal antibody NEA9301 against gp120 and an alkaline phosphatase conjugated secondary antibody. Cells were incubated with 0.33 mg/ml NBT and 0.16 mg/ml BCIP in AP-buffer and finally overlaid with 1% agarose in PBS. Positive plaques were picked and resuspended in 100 µl Tris pH 9.0. The plaque purification was repeated once. To produce high titer stocks the infection was slowly scaled up. Finally, one large plate of Hela cells was infected with half of the virus of the previous round. Infected cells were detached in 3 ml of PBS, lysed with a Dounce homogenizer and cleared from larger debris by centrifugation. VPE-8 recombinant vaccinia stocks were kindly provided by the AIDS repository, Rockville, Md., and express HIV-1 IIIB gp120 under the 7.5 mixed early/late promoter (Earl et al., *J. Virol.*, 65:31, 1991). In all experiments with recombinant vaccina cells were infected at a multiplicity of infection of at least 10.

The following solution was used in this procedure: AP buffer (100 mM Tris HCl, pH 9.5, 100 mM NaCl, 5 mM $MgCl_2$)

Cell culture

The monkey kidney carcinoma cell lines CV1 and Cos7, the human kidney carcinoma cell line 293T, and the human cervix carcinoma cell line Hela were obtained from the American Tissue Typing Collection and were maintained in supplemented IMDM. They were kept on 10 cm tissue culture plates and typically split 1:5 to 1:20 every 3 to 4 days.

The following medium was used in this procedure: Supplemented IMDM (90% Iscove's modified Dulbecco Medium, 10% calf serum, iron-complemented, heat inactivated 30 min 56° C., 0.3 mg/ml L-glutamine, 25 μg/ml gentamycin 0.5 mM β-mercaptoethanol (pH adjusted with 5M NaOH, 0.5 ml)).

Transfection

Calcium phosphate transfection of 293T cells was performed by slowly adding and under vortexing 10 μg plasmid DNA in 250 μl 0.25M $CaCl_2$ to the same volume of 2× HEBS buffer while vortexing. After incubation for 10 to 30 min at room temperature the DNA precipitate was added to a small dish of 50 to 70% confluent cells. In cotransfection experiments with rev, cells were transfected with 10 μg gp120IIIb, gp120IIIbrre, syngp120mnrre or rTHY-1enveg1rre and 10 μg of pCMVrev or CDM7 plasmid DNA.

The following solutions were used in this procedure: 2× HEBS buffer (280 mM NaCl, 10 mM KCl, 1.5 mM sterile filtered); 0.25 mM $CaCl_2$ (autoclaved).

Immunoprecipitation

After 48 to 60 hours medium was exchanged and cells were incubated for additional 12 hours in Cys/Met-free medium containing 200 μCi of $^{35}S$-translabel. Supernatants were harvested and spun for 15 min at 3000 rpm to remove debris. After addition of protease inhibitors leupeptin, aprotinin and PMSF to 2.5 μg/ml, 50 μg/ml, 100 μg/ml respectively, 1 ml of supernatant was incubated with either 10 μl of packed protein A sepharose alone (rTHY-1enveg1rre) or with protein A sepharose and 3 μg of a purified CD4/immunoglobulin fusion protein (kindly provided by Behring) (all gp120 constructs) at 4° C. for 12 hours on a rotator. Subsequently the protein A beads were washed 5 times for 5 to 15 min each time. After the final wash 10 μl of loading buffer containing was added, samples were boiled for 3 min and applied on 7% (all gp120 constructs) or 10% (rTHY-1enveg1rre) SDS polyacrylamide gels (Tris pH 8.8 buffer in the resolving, Tris pH 6.8 buffer in the stacking gel, Tris-glycine running buffer, Maniatis et al. 1989). Gels were fixed in 10% acetic acid and 10% methanol, incubated with Amplify for 20 min, dried and exposed for 12 hours.

The following buffers and solutions were used in this procedure: Wash buffer (100 mM Tris, pH 7.5, 150 mM NaCl, 5 mM $CaCl_2$, 1% NP-40); 5× Running Buffer (125 mM Tris, 1.25M Glycine, 0.5% SDS); Loading buffer (10% glycerol, 4% SDS, 4% β-mercaptoethanol, 0.02% bromphenol blue).

Immunofluorescence 293T cells were transfected by calcium phosphate coprecipitation and analyzed for surface THY-1 expression after 3 days. After detachment with 1 mM EDTA/PBS, cells were stained with the monoclonal antibody OX-7 in a dilution of 1:250 at 4° C. for 20 min, washed with PBS and subsequently incubated with a 1:500 dilution of a FITC-conjugated goat anti-mouse immunoglobulin antiserum. Cells were washed again, resuspended in 0.5 ml of a fixing solution, and analyzed on an EPICS XL cytofluorometer (Coulter).

The following solutions were used in this procedure: PBS (137 mM NaCl, 2.7 mM KCl, 4.3 mM $Na_2HPO_4$, 1.4 mM $KH_2PO_4$, pH adjusted to 7.4); Fixing solution (2% formaldehyde in PBS).

ELISA

The concentration of gp120 in culture supernatants was determined using CD4-coated ELISA plates and goat anti-gp120 antisera in the soluble phase. Supernatants of 293T cells transfected by calcium phosphate were harvested after 4 days, spun at 3000 rpm for 10 min to remove debris and incubated for 12 hours at 4° C. on the plates. After 6 washes with PBS 100 μl of goat anti-gp120 antisera diluted 1:200 were added for 2 hours. The plates were washed again and incubated for 2 hours with a peroxidase-conjugated rabbit anti-goat IgG antiserum 1:1000. Subsequently the plates were washed and incubated for 30 min with 100 μl of substrate solution containing 2 mg/ml o-phenylenediamine in sodium citrate buffer. The reaction was finally stopped with 100 μl of 4M sulfuric acid. Plates were read at 490 nm with a Coulter microplate reader. Purified recombinant gp120IIIb was used as a control. The following buffers and solutions were used in this procedure: Wash buffer (0.1% NP40 in PBS); Substrate solution (2 mg/ml o-phenylenediamine in sodium citrate buffer).

Use

The synthetic genes of the invention are useful for expressing a protein normally expressed in mammalian cells in cell culture (e.g. for commercial production of human proteins such as hGH, TPA, Factor VII, and Factor IX). The synthetic genes of the invention are also useful for gene therapy.

SEQUENCE LISTING ( 1 ) GENERAL INFORMATION:

( i i i ) NUMBER OF SEQUENCES: 37

( 2 ) INFORMATION FOR SEQ ID NO:1:

-continued ( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:1:

CGCGGGCTAG CCACCGAGAA GCTG 24

( 2 ) INFORMATION FOR SEQ ID NO:2:

( i ) SEQUENCE CHARACTERISTICS:
( A ) LENGTH: 196 base pairs
( B ) TYPE: nucleic acid
( C ) STRANDEDNESS: single
( D ) TOPOLOGY: linear ( x i ) SEQUENCE DESCRIPTION: SEQ ID NO:2:

ACCGAGAAGC TGTGGGTGAC CGTGTACTAC GGCGTGCCCG TGTGGAAGAG AGGCCACCAC 60

CACCCTGTTC TGCGCCAGCG ACGCCAAGGC GTACGACACC GAGGTGCACA ACGTGTGGGC 120

CACCCAGGCG TGCGTGCCCA CCGACCCCAA CCCCCAGGAG GTGGAGCTCG TGAACGTGAC 180

CGAGAACTTC AACATG 196

( 2 ) INFORMATION FOR SEQ ID NO:3:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:3:

CCACCATGTT GTTCTTCCAC ATGTTGAAGT TCTC 34

( 2 ) INFORMATION FOR SEQ ID NO:4:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:4:

GACCGAGAAC TTCAACATGT GGAAGAACAA CAT 33

( 2 ) INFORMATION FOR SEQ ID NO:5:

( i ) SEQUENCE CHARACTERISTICS:
( A ) LENGTH: 192 base pairs
( B ) TYPE: nucleic acid
( C ) STRANDEDNESS: single
( D ) TOPOLOGY: linear ( x i ) SEQUENCE DESCRIPTION: SEQ ID NO:5:

TGGAAGAACA ACATGGTGGA GCAGATGCAT GAGGACATCA TCAGCCTGTG GGACCAGAGC 60

CTGAAGCCCT GCGTGAAGCT GACCCCCTGT GCGTGACCTG AACTGCACCG ACCTGAGGAA 120

CACCACCAAC ACCAACACAG CACCGCCAAC AACAACAGCA ACAGCGAGGG CACCATCAAG 180

GGCGGCGAGA TG 192

( 2 ) INFORMATION FOR SEQ ID NO:6:

( i ) SEQUENCE CHARACTERISTICS:
( A ) LENGTH: 33 base pairs
( B ) TYPE: nucleic acid -continued ( C ) STRANDEDNESS: single
( D ) TOPOLOGY: linear ( x i ) SEQUENCE DESCRIPTION: SEQ ID NO:6:

GTTGAAGCTG CAGTTCTTCA TCTCGCCGCC CTT 33

( 2 ) INFORMATION FOR SEQ ID NO:7:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:7:

GAAGAACTGC AGCTTCAACA TCACCACCAG C 31

( 2 ) INFORMATION FOR SEQ ID NO:8:

( i ) SEQUENCE CHARACTERISTICS:
( A ) LENGTH: 195 base pairs
( B ) TYPE: nucleic acid
( C ) STRANDEDNESS: single
( D ) TOPOLOGY: linear ( x i ) SEQUENCE DESCRIPTION: SEQ ID NO:8:

AACATCACCA CCAGCATCCG CGACAAGATG CAGAAGGAGT ACGCCCTGCT GTACAAGCTG 60

GATATCGTGA GCATCGACAA CGACAGCACC AGCTACCGCC TGATCTCCTG CAACACCAGC 120

GTGATCACCC AGGCCTGCCC CAAGATCAGC TTCGAGCCCA TCCCCATCCA CTACTGCGCC 180

CCCGCCGGCT TCGCC 195

( 2 ) INFORMATION FOR SEQ ID NO:9:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:9:

GAACTTCTTG TCGGCGGCGA AGCCGGCGGG 30

( 2 ) INFORMATION FOR SEQ ID NO:10:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( x i ) SEQUENCE DESCRIPTION: SEQ ID NO:10:

GCGCCCCCGC CGGCTTCGCC ATCCTGAAGT GCAACGACAA GAAGTTC 47

( 2 ) INFORMATION FOR SEQ ID NO:11:

( i ) SEQUENCE CHARACTERISTICS:
( A ) LENGTH: 198 base pairs
( B ) TYPE: nucleic acid
( C ) STRANDEDNESS: single
( D ) TOPOLOGY: linear ( x i ) SEQUENCE DESCRIPTION: SEQ ID NO:11:

GCCGACAAGA AGTTCAGCGG CAAGGGCAGC TGCAAGAACG TGAGCACCGT GCAGTGCACC 60

CACGGCATCC GGCCGGTGGT GAGCACCCAG CTCCTGCTGA ACGGCAGCCT GGCCGAGGAG 120

-continued

GAGGTGGTGA TCCGCAGCGA GAACTTCACC GACAACGCCA AGACCATCAT CGTGCACCTG 180

AATGAGAGCG TGCAGATC 198

( 2 ) INFORMATION FOR SEQ ID NO:12:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:12:

AGTTGGGACG CGTGCAGTTG ATCTGCACGC TCTC 34

( 2 ) INFORMATION FOR SEQ ID NO:13:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:13:

GAGAGCGTGC AGATCAACTG CACGCGTCCC 30

( 2 ) INFORMATION FOR SEQ ID NO:14:

( i ) SEQUENCE CHARACTERISTICS:
( A ) LENGTH: 120 base pairs
( B ) TYPE: nucleic acid
( C ) STRANDEDNESS: single
( D ) TOPOLOGY: linear ( x i ) SEQUENCE DESCRIPTION: SEQ ID NO:14:

AACTGCACGC GTCCCAACTA CAACAAGCGC AAGCGCATCC ACATCGGCCC CGGGCGCGCC 60

TTCTACACCA CCAAGAACAT CATCGGCACC ATCCTCCAGG CCCACTGCAA CATCTCTAGA 120

( 2 ) INFORMATION FOR SEQ ID NO:15:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:15:

GTCGTTCCAC TTGGCTCTAG AGATGTTGCA 30

( 2 ) INFORMATION FOR SEQ ID NO:16:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:16:

GCAACATCTC TAGAGCCAAG TGGAACGAC 29

( 2 ) INFORMATION FOR SEQ ID NO:17:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( x i ) SEQUENCE DESCRIPTION: SEQ ID NO:17:

GCCAAGTGGA ACGACACCCT GCGCCAGATC GTGAGCAAGC TGAAGGAGCA GTTCAAGAAC 60

AAGACCATCG TGTTCACCAG AGCAGCGGCG GCGACCCCGA GATCGTGATG CACAGCTTCA 120

ACTGCGGCGG C 131

( 2 ) INFORMATION FOR SEQ ID NO:18:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:18:

GCAGTAGAAG AATTCGCCGC CGCAGTTGA 29

( 2 ) INFORMATION FOR SEQ ID NO:19:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:19:

TCAACTGCGG CGGCGAATTC TTCTACTGC 29

( 2 ) INFORMATION FOR SEQ ID NO:20:

( i ) SEQUENCE CHARACTERISTICS:
( A ) LENGTH: 195 base pairs
( B ) TYPE: nucleic acid
( C ) STRANDEDNESS: single
( D ) TOPOLOGY: linear ( x i ) SEQUENCE DESCRIPTION: SEQ ID NO:20:

GGCGAATTCT TCTACTGCAA CACCAGCCCC CTGTTCAACA GCACCTGGAA CGGCAACAAC 60

ACCTGGAACA ACACCACCGG CAGCAACAAC AATATTACCC TCCAGTGCAA GATCAAGCAG 120

ATCATCAACA TGTGGCAGGA GGTGGGCAAG GCCATGTACG CCCCCCCCAT CGAGGGCCAG 180

ATCCGGTGCA GCAGC 195

( 2 ) INFORMATION FOR SEQ ID NO:21:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:21:

GCAGACCGGT GATGTTGCTG CTGCACCGGA TCTGGCCCTC 40

( 2 ) INFORMATION FOR SEQ ID NO:22:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( x i ) SEQUENCE DESCRIPTION: SEQ ID NO:22:

CGAGGGCCAG ATCCGGTGCA GCAGCAACAT CACCGGTCTG 40

-continued ( 2 ) INFORMATION FOR SEQ ID NO:23:

( i ) SEQUENCE CHARACTERISTICS:
( A ) LENGTH: 242 base pairs
( B ) TYPE: nucleic acid
( C ) STRANDEDNESS: single
( D ) TOPOLOGY: linear ( x i ) SEQUENCE DESCRIPTION: SEQ ID NO:23:

AACATCACCG GTCTGCTGCT GCTGCTGACC CGGACGGCGG CAAGGACACC GACACCAACG 60

ACACCGAAAT CTTCCGCGAC GGCGGCAAGG ACACCAACGA CACCGAAATC TTCCGCCCCG 120

GCGGCGGCGA CATGCGCGAC AACTGGAGAT CTGAGCTGTA CAAGTACAAG GTGGTGACGA 180

TCGAGCCCCT GGGCGTGGCC CCCACCAAGG CCAAGCGCGC GGTGGTGCAG CGCGAGAAGC 240

GC 242

( 2 ) INFORMATION FOR SEQ ID NO:24:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( x i ) SEQUENCE DESCRIPTION: SEQ ID NO:24:

CGCGGGCGGC CGCTTTAGCG CTTCTCGCGC TGCACCAC 38

( 2 ) INFORMATION FOR SEQ ID NO:25:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( x i ) SEQUENCE DESCRIPTION: SEQ ID NO:25:

CGCGGGGGAT CCAAGCTTAC CATGATTCCA GTAATAAGT 39

( 2 ) INFORMATION FOR SEQ ID NO:26:

( i ) SEQUENCE CHARACTERISTICS:
( A ) LENGTH: 165 base pairs
( B ) TYPE: nucleic acid
( C ) STRANDEDNESS: single
( D ) TOPOLOGY: linear ( x i ) SEQUENCE DESCRIPTION: SEQ ID NO:26:

ATGAATCCAG TAATAAGTAT AACATTATTA TTAAGTGTAT TACAAATGAG TAGAGGACAA 60

AGAGTAATAA GTTTAACAGC ATCTTTAGTA AATCAAAATT TGAGATTAGA TTGTAGACAT 120

GAAAATAATA CAAATTTGCC AATACAACAT GAATTTTCAT TAACG 165

( 2 ) INFORMATION FOR SEQ ID NO:27:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:27:

CGCGGGGAAT TCACGCGTTA ATGAAAATTC ATGTTG 36

( 2 ) INFORMATION FOR SEQ ID NO:28:

( i ) SEQUENCE CHARACTERISTICS:

( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:28:

CGCGGATCCA CGCGTGAAAA AAAAAAACAT 30

( 2 ) INFORMATION FOR SEQ ID NO:29:

( i ) SEQUENCE CHARACTERISTICS:
( A ) LENGTH: 149 base pairs
( B ) TYPE: nucleic acid
( C ) STRANDEDNESS: single
( D ) TOPOLOGY: linear ( x i ) SEQUENCE DESCRIPTION: SEQ ID NO:29:

CGTGAAAAAA AAAAACATGT ATTAAGTGGA ACATTAGGAG TACCAGAACA TACATATAGA 60

AGTAGAGTAA TTTGTTTAGT GATAGATTCA TAAAAGTATT AACATTAGCA AATTTTACAA 120

CAAAAGATGA AGGAGATTAT ATGTGTGAG 149

( 2 ) INFORMATION FOR SEQ ID NO:30:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:30:

CGCGAATTCG AGCTCACACA TATAATCTCC 30

( 2 ) INFORMATION FOR SEQ ID NO:31:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:31:

CGCGGATCCG AGCTCAGAGT AAGTGGACAA 30

( 2 ) INFORMATION FOR SEQ ID NO:32:

( i ) SEQUENCE CHARACTERISTICS:
( A ) LENGTH: 170 base pairs
( B ) TYPE: nucleic acid
( C ) STRANDEDNESS: single
( D ) TOPOLOGY: linear ( x i ) SEQUENCE DESCRIPTION: SEQ ID NO:32:

CTCAGAGTAA GTGGACAAAA TCCAACAAGT AGTAATAAAA CAATAAATGT AATAAGAGAT 60

AAATTAGTAA AATGTGAGGA ATAAGTTTAT TAGTACAAAA TACAAGTTGG TTATTATTAT 120

TATTATTAAG TTTAAGTTTT TTACAAGCAA CAGATTTTAT AAGTTTATGA 170

( 2 ) INFORMATION FOR SEQ ID NO:33:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:33:

-continued

CGCGAATTCG CGGCCGCTTC ATAAACTTAT AAAATC 36

( 2 ) INFORMATION FOR SEQ ID NO:34:

( i ) SEQUENCE CHARACTERISTICS:
( A ) LENGTH: 1632 base pairs
( B ) TYPE: nucleic acid
( C ) STRANDEDNESS: single
( D ) TOPOLOGY: linear ( x i ) SEQUENCE DESCRIPTION: SEQ ID NO:34:

CTCGAGATCC ATTGTGCTCT AAAGGAGATA CCCGGCCAGA CACCCTCACC TGCGGTGCCC 60

AGCTGCCCAG GCTGAGGCAA GAGAAGGCCA GAAACCATGC CCATGGGGTC TCTGCAACCG 120

CTGGCCACCT TGTACCTGCT GGGGATGCTG GTCGCTTCCG TGCTAGCCAC CGAGAAGCTG 180

TGGGTGACCG TGTACTACGG CGTGCCCGTG TGGAAGGAGG CCACCACCAC CCTGTTCTGC 240

GCCAGCGACG CCAAGGCGTA CGACACCGAG GTGCACAACG TGTGGGCCAC CCAGGCGTGC 300

GTGCCCACCG ACCCCAACCC CCAGGAGGTG GAGCTCGTGA ACGTGACCGA GAACTTCAAC 360

ATGTGGAAGA ACAACATGGT GGAGCAGATG CATGAGGACA TCATCAGCCT GTGGGACCAG 420

AGCCTGAAGC CCTGCGTGAA GCTGACCCCC CTGTGCGTGA CCCTGAACTG CACCGACCTG 480

AGGAACACCA CCAACACCAA CAACAGCACC GCCAACAACA ACAGCAACAG CGAGGGCACC 540

ATCAAGGGCG GCGAGATGAA CAACTGCAGC TTCAACATCA CCACCAGCAT CCGCGACAAG 600

ATGCAGAAGG AGTACGCCCT GCTGTACAAG CTGGATATCG TGAGCATCGA CAACGACAGC 660

ACCAGCTACC GCCTGATCTC CTGCAACACC AGCGTGATCA CCCAGGCCTG GCCCAAGATC 720

AGCTTCGAGC CCATCCCCAT CCACTACTGC GCCCCCGCCG GCTTCGCCAT CCTGAAGTGC 780

AACGACAAGA AGTTCAGCGG CAAGGGCAGC TGCAAGAACG TGAGCACCGT GCAGTGCACC 840

CACGGCATCC GGCCGGTGGT GAGCACCCAG CTCCTGCTGA ACGGCAGCCT GGCCGAGGAG 900

GAGGTGGTGA TCCGCAGCGA GAACTTCACC GACAACGCCA AGACCATCAT CGTGCACCTG 960

AATGAGAGCG TGCAGATCAA CTGCACGCGT CCCAACTACA ACAAGCGCAA GCGCATCCAC 1020

ATCGGCCCCG GGCGCGCCTT CTACACCACC AAGAACATCA TCGGCACCAT CCGCCAGGCC 1080

CACTGCAACA TCTCTAGAGC CAAGTGGAAC GACACCCTGC GCCAGATCGT GAGCAAGCTG 1140

AAGGAGCAGT TCAAGAACAA GACCATCGTG TTCAACCAGA GCAGCGGCGG CGACCCCGAG 1200

ATCGTGATGC ACAGCTTCAA CTGCGGCGGC GAATTCTTCT ACTGCAACAC CAGCCCCCTG 1260

TTCAACAGCA CCTGGAACGG CAACAACACC TGGAACAACA CCACCGGCAG CAACAACAAT 1320

ATTACCCTCC AGTGCAAGAT CAAGCAGATC ATCAACATGT GGCAGGAGGT GGGCAAGGCC 1380

ATGTACGCCC CCCCCATCGA GGGCCAGATC CGGTGCAGCA GCAACATCAC CGGTCTGCTG 1440

CTGACCCGCG ACGGCGGCAA GGACACCGAC ACCAACGACA CCGAAATCTT CCGCCCCGGC 1500

GGCGGCGACA TGCGCGACAA CTGGAGATCT GAGCTGTACA AGTACAAGGT GGTGACGATC 1560

GAGCCCCTGG GCGTGGCCCC CACCAAGGCC AAGCGCCGCG TGGTGCAGCG CGAGAAGCGC 1620

TAAAGCGGCC GC 1632

( 2 ) INFORMATION FOR SEQ ID NO:35:

( i ) SEQUENCE CHARACTERISTICS:
( A ) LENGTH: 2481 base pairs
( B ) TYPE: nucleic acid
( C ) STRANDEDNESS: single
( D ) TOPOLOGY: linear ( x i ) SEQUENCE DESCRIPTION: SEQ ID NO:35:

-continued

```
ACCGAGAAGC TGTGGGTGAC CGTGTACTAC GGCGTGCCCG TGTGGAAGGA GGCCACCACC   60
ACCCTGTTCT GCGCCAGCGA CGCCAAGGCG TACGACACCG AGGTGCACAA CGTGTGGGCC  120
ACCCAGGCGT GCGTGCCCAC CGACCCCAAC CCCCAGGAGG TGGAGCTCGT GAACGTGACC  180
GAGAACTTCA ACATGTGGAA GAACAACATG CTGGAGCAGA TGCATGAGGA CATCATCAGC  240
CTGTGGGACC AGAGCCTGAA GCCCTGCGTG AAGCTGACCC CCCTGTGCGT GACCCTGAAC  300
TGCACCGACC TGAGGAACAC CACCAACACC AACAACAGCA CCGCCAACAA CAACAGCAAC  360
AGCGAGGGCA CCATCAAGGG CGGCGAGATG AAGAACTGCA GCTTCAACAT CACCACCAGC  420
ATCCGCGACA AGATGCAGAA GGAGTACGCC CTGCTGTACA AGCTGGATAT CGTGAGCATC  480
CACAACGACA GCACCAGCTA CCGCCTGATC TCCTGCAACA CCAGCGTGAT CACCCAGGCC  540
TGCCCCAAGA TCAGCTTCGA GCCCATCCCC ATCCACTACT GCGCCCCCGC CGGCTTCGCC  600
ATCCTGAAGT GCAACGACAA GAAGTTCAGC GGCAAGGGCA GCTGCAAGAA CGTGACCACC  660
GTGCAGTGCA CCCACGGCAT CCGGCCGGTG GTGAGCACCC AGCTCCTGCT GAACGGCAGC  720
CTGGCCGAGG AGGAGGTGGT GATCCGCAGC GAGAACTTCA CCGACAACGC CAAGACCATC  780
ATCGTGCACC TGAATGAGAG CGTGCAGATC AACTGCACGC GTCCCAACTA CAACAAGCGC  840
AAGCGCATCC ACATCGGCCC CGGGCGCGCC TTCTACACCA CCAAGAACAT CATCGGCACC  900
ATCCGCCAGG CCCACTGCAA CATCTCTAGA GCCAAGTGGA ACGACACCCT GCGCCAGATC  960
GTGAGCAAGC TGAAGGAGCA GTTCAAGAAC AAGACCATCG TGTTCAACCA GAGCAGCGGC 1020
GGCGACCCCG AGATCGTGAT GCACAGCTTC AACTGCGGCG GCGAATTCTT CTACTGCAAC 1080
ACCAGCCCCC TGTTCAACAG CACCTGGAAC GGCAACAACA CCTGGAACAA CACCACCGGC 1140
AGCAACAACA ATATTACCCT CCAGTGCAAG ATCAAGCAGA TCATCAACAT GTGGCAGGAG 1200
GTGGGCAAGG CCATGTACGC CCCCCCCATC GAGGGCCAGA TCCGGTGCAG CAGCAACATC 1260
ACCGGTCTGC TGCTGACCCG CGACGGCGGC AAGGACACCG ACACCAACGA CACCGAAATC 1320
TTCCGCCCCG GCGGCGGCGA CATGCGCGAC AACTGGAGAT CTGAGCTGTA CAAGTACAAG 1380
GTGGTGACGA TCGAGCCCCT GGGCGTGGCC CCCACCAAGG CCAAGCGCCG CGTGGTGCAG 1440
CGCGAGAAGC GGGCCGCCAT CGGCGCCCTG TTCCTGGGCT TCCTGGGGGC GGCGGGCAGC 1500
ACCATGGGGG CCGCCAGCGT GACCCTGACC GTGCAGGCCC GCCTGCTCCT GAGCGGCATC 1560
GTGCAGCAGC AGAACAACCT CCTCCGCGCC ATCGAGGCCC AGCAGCATAT GCTCCAGCTC 1620
ACCGTGTGGG GCATCAAGCA GCTCCAGGCC CGCGTGCTGG CCGTGGAGCG CTACCTGAAG 1680
GACCAGCAGC TCCTGGGCTT CTGGGGCTGC TCCGGCAAGC TGATCTGCAC CACCACGGTA 1740
CCCTGGAACG CCTCCTGGAG CAACAAGAGC CTGGACGACA TCTGGAACAA CATGACCTGG 1800
ATGCAGTGGG AGCGCGAGAT CGATAACTAC ACCAGCCTGA TCTACAGCCT GCTGGAGAAG 1860
AGCCAGACCC AGCAGGAGAA GAACGAGCAG GAGCTGCTGG AGCTGGACAA CTGGGCGAGC 1920
CTGTGGAACT GGTTCGACAT CACCAACTGG CTGTGGTACA TCAAAATCTT CATCATGATT 1980
GTGGGCGGCC TGGTGGGCCT CCGCATCGTG TTCGCCGTGC TGAGCATCGT GAACCGCGTG 2040
CGCCAGGGCT ACAGCCCCCT GAGCCTCCAG ACCCGGCCCC CCGTGCCGCG CGGGCCCGAC 2100
CGCCCCGAGG GCATCGAGGA GGAGGGCGGC GAGCGCGACC GCGACACCAG CGGCAGGCTC 2160
GTGCACGGCT TCCTGGCGAT CATCTGGGTC GACCTCCGCA GCCTGTTCCT GTTCAGCTAC 2220
CACCACCGCG ACCTGCTGCT GATCGCCGCC CGCATCGTGG AACTCCTAGG CCGCCGCGGC 2280
TGGGAGGTGC TGAAGTACTG GTGGAACCTC CTCCAGTATT GGAGCCAGGA GCTGAAGTCC 2340
AGCGCCGTGA GCCTGCTGAA CGCCACCGCC ATCGCCGTGG CCGAGGGCAC CGACCGCGTG 2400
```

-continued

| | | | | | | |
|---|---|---|---|---|---|---|
| ATCGAGGTGC | TCCAGAGGGC | CGGGAGGGCG | ATCCTGCACA | TCCCCACCCG | CATCCGCCAG | 2460 |
| GGGCTCGAGA | GGGCGCTGCT | G | | | | 2481 |

( 2 ) INFORMATION FOR SEQ ID NO:36:

( i ) SEQUENCE CHARACTERISTICS:
( A ) LENGTH: 486 base pairs
( B ) TYPE: nucleic acid
( C ) STRANDEDNESS: single
( D ) TOPOLOGY: linear ( x i ) SEQUENCE DESCRIPTION: SEQ ID NO:36:

| | | | | | | |
|---|---|---|---|---|---|---|
| ATGAATCCAG | TAATAAGTAT | AACATTATTA | TTAAGTGTAT | TACAAATGAG | TAGAGGACAA | 60 |
| AGAGTAATAA | GTTTAACAGC | ATGTTTAGTA | AATCAAAATT | TGAGATTAGA | TTGTAGACAT | 120 |
| GAAAATAATA | CACCTTTGCC | AATACAACAT | GAATTTTCAT | TAACGCGTGA | AAAAAAAAAA | 180 |
| CATGTATTAA | GTGGAACATT | AGGAGTACCA | GAACATACAT | ATAGAAGTAG | AGTAAATTTG | 240 |
| TTTAGTGATA | GATTCATAAA | AGTATTAACA | TTAGCAAATT | TTACAACAAA | AGATGAAGGA | 300 |
| GATTATATGT | GTGAGCTCAG | AGTAAGTGGA | CAAAATCCAA | CAAGTAGTAA | TAAAACAATA | 360 |
| AATGTAATAA | GAGATAAATT | AGTAAAATGT | GGAGGAATAA | GTTTATTAGT | ACAAAATACA | 420 |
| AGTTGGTTAT | TATTATTATT | ATTAAGTTTA | AGTTTTTTAC | AAGCAACAGA | TTTTATAAGT | 480 |
| TTATGA | | | | | | 486 |

( 2 ) INFORMATION FOR SEQ ID NO:37:

( i ) SEQUENCE CHARACTERISTICS:
( A ) LENGTH: 485 base pairs
( B ) TYPE: nucleic acid
( C ) STRANDEDNESS: single
( D ) TOPOLOGY: linear ( x i ) SEQUENCE DESCRIPTION: SEQ ID NO:37:

| | | | | | | |
|---|---|---|---|---|---|---|
| ATGAACCCAG | TCATCAGCAT | CACTCTCCTG | CTTTCAGTCT | TGCAGATGTC | CCGAGGACAG | 60 |
| AGGGTGATCA | GCCTGACAGC | CTGCCTGGTG | AACAGAACCT | TCGACTGGAC | TGCCGTCATG | 120 |
| AGAATAACAC | CAACTTGCCC | ATCCAGCATG | AGTTCAGCCT | GACCCGAGAG | AAGAAGAAGC | 180 |
| ACGTGCTGTC | AGGCACCCTG | GGGGTTCCCG | AGCACACTTA | CCGCTCCCGC | GTCAACCTTT | 240 |
| TCAGTGACCG | CTTTATCAAG | GTCCTTACTC | TAGCCAACTT | GACCACCAAG | GATGAGGGCG | 300 |
| ACTACATGTG | TGAACTTCGA | GTCTCGGGCC | AGAATCCCAC | AAGCTCCAAT | AAAACTATCA | 360 |
| ATGTGATCAG | AGACAAGCTG | GTCAAGTGTG | GTGGCATAAG | CCTGCTGGTT | CAAAACACTT | 420 |
| CCTGGCTGCT | GCTGCTCCTG | CTTTCCCTCT | CCTTCCTCCA | AGCCACGGAC | TTCATTTCTC | 480 |
| TGTGA | | | | | | 485 |

What is claimed is:

1. A synthetic gene encoding a protein normally expressed in mammalian cells wherein at least one non-preferred or less preferred codon in the natural gene encoding said protein has been replaced by a preferred codon encoding the same amino acid, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said protein in a mammalian host cell at a level which is at least 110% of that expressed by said natural gene in an in vitro mammalian cell culture system under identical conditions.

2. The synthetic gene of claim 1 wherein said synthetic gene permits the expression of said protein in a mammalian host cell at a level which is at least 150% of that expressed by said natural gene in an in vitro mammalian cell culture system under identical conditions.

3. The synthetic gene of claim 1 wherein said synthetic gene permits the expression of said protein in a mammalian host cell at a level which is at least 200% of that expressed by said natural gene in an in vitro mammalian cell culture system under identical conditions.

4. The synthetic gene of claim 1 wherein said synthetic gene permits the expression of said protein in a mammalian host cell at a level which is at least 500% of that expressed by said natural gene in an in vitro mammalian cell culture system under identical conditions.

5. The synthetic gene of claim 1 wherein said synthetic gene permits the expression of said protein in a mammalian host cell at a level which is at least ten times that expressed by said natural gene in an in vitro mammalian cell culture system under identical conditions.

6. The synthetic gene of claim 1 wherein at least 10% of the codons in said natural gene are non-preferred codons.

7. The synthetic gene of claim 1 wherein at least 50% of the codons in said natural gene are non-preferred codons.

8. The synthetic gene of claim 1 wherein at least 50% of the non-preferred codons and less preferred codons present in said natural gene have been replaced by preferred codons.

9. The synthetic gene of claim 1 wherein at least 90% of the non-preferred codons and less preferred codons present in said natural gene have been replaced by preferred codons.

10. The synthetic gene of claim 1 wherein said protein is a retroviral protein.

11. The synthetic gene of claim 1 wherein said protein is a human protein.

12. A synthetic gene encoding a lentiviral protein wherein at least one non-preferred or less preferred codon in the natural gene encoding said lentiviral protein has been replaced by a preferred codon encoding the same amino acid, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said lentiviral protein in a mammalian host cell at a level which is at least 110% of that expressed by said natural gene in an in vitro mammalian cell culture system under identical conditions.

13. The synthetic gene of claim 12 wherein said lentiviral protein is an HIV protein.

14. The synthetic gene of claim 13 wherein said lentiviral protein is selected from the group consisting of gag, pol, and env.

15. The synthetic gene of claim 13 wherein said protein is gp120.

16. The synthetic gene of claim 13 wherein said protein is gp160.

17. A method for preparing a synthetic gene encoding a protein normally expressed by mammalian cells, comprising identifying non-preferred and less preferred codons in the natural gene encoding said protein and replacing one or more of said non-preferred and less preferred codons with a preferred codon encoding the same amino acid as the replaced codon, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said protein in a mammalian host cell at a level which is at least 110% of that expressed by said natural gene in an in vitro mammalian cell culture system under identical conditions.

18. A method for preparing a synthetic gene encoding a lentiviral protein, comprising identifying non-preferred and less preferred codons in the natural gene encoding said lentiviral protein and replacing one or more of said non-preferred and less preferred codons with a preferred codon encoding the same amino acid as the replaced codon, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said lentiviral protein in a mammalian host cell at a level which is at least 110% of that expressed by said natural gene in an in vitro mammalian cell culture system under identical conditions.

* * * * *

UNITED STATES PATENT AND TRADEMARK OFFICE

Certificate

Patent No. 5,786,464 Patented: July 28, 1998

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Brian Seed, Boston, Massachusetts and Jurgen Haas, Muenchen, Germany.

Signed and Sealed this Ninth Day of November, 1999.

PONNATHAPURA ACHUTAMURTHY
*Supervisory Patent Examiner*
Art Unit 1652

UNITED STATES PATENT AND TRADEMARK OFFICE

CERTIFICATE OF CORRECTION

PATENT NO. : 5,786,464 C1
APPLICATION NO. : 90/011382
DATED : July 28, 1998
INVENTOR(S) : Seed et al.

It is certified that error appears in the above-identified patent and that said Letters Patent is hereby corrected as shown below:

In the Ex Parte Reexamination Certificate, cover page, under (73) Assignee, replace "National Institutes of Health (NIH), U.S. Dept. of Health and Human Services (DHHS), Washington, DC (US)" with --The General Hospital Corporation, Boston, MA--.

Signed and Sealed this
Twenty-fifth Day of September, 2012

David J. Kappos
*Director of the United States Patent and Trademark Office*

US005786464C1

(12) EX PARTE REEXAMINATION CERTIFICATE (8978th)

United States Patent

Seed et al.

(10) Number: US 5,786,464 C1

(45) Certificate Issued: Apr. 24, 2012

(54) OVEREXPRESSION OF MAMMALIAN AND VIRAL PROTEINS

(75) Inventors: Brian Seed, Boston, MA (US); Jurgen Haas, Munich (DE)

(73) Assignee: National Institutes of Health (NIH), U.S. Dept. of Health and Human Services (DHHS), Washington, DC (US)

Reexamination Request:

No. 90/011,382, Dec. 9, 2010

Reexamination Certificate for:

| | |
|---|---|
| Patent No.: | **5,786,464** |
| Issued: | **Jul. 28, 1998** |
| Appl. No.: | **08/324,243** |
| Filed: | **Sep. 19, 1994** |

Certificate of Correction issued Nov. 9, 1999.

(51) Int. Cl.

| | |
|---|---|
| ***C07K 14/705*** | (2006.01) |
| ***C07K 14/16*** | (2006.01) |
| ***C07K 14/005*** | (2006.01) |
| ***C07K 14/435*** | (2006.01) |
| ***C12N 15/67*** | (2006.01) |
| ***C12N 15/85*** | (2006.01) |

(52) U.S. Cl. .................. 536/23.5; 435/252.3; 435/69.1; 435/91.5; 536/23.72

(58) Field of Classification Search ........................ None

See application file for complete search history.

(56) References Cited

To view the complete listing of prior art documents cited during the proceeding for Reexamination Control Number 90/011,382, please refer to the USPTO's public Patent Application Information Retrieval (PAIR) system under the Display References tab.

*Primary Examiner*—Padmashri Ponnaluri

(57) ABSTRACT

The invention features a synthetic gene encoding a protein normally expressed in mammalian cells wherein at least one non-preferred or less preferred codon in the natural gene encoding the mammalian protein has been replaced by a preferred codon encoding the same amino acid.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 8 is cancelled.

Claims 1, 12, 17 and 18 are determined to be patentable as amended.

Claims 2-7, 9-11 and 13-16, dependent on an amended claim, are determined to be patentable.

New claims 19-30 are added and determined to be patentable.

1. A synthetic gene encoding a protein normally expressed in mammalian cells wherein at least [one non-preferred or less preferred codon in the natural gene encoding said protein has] *50% of the non-preferred codons and less preferred codons present in said natural gene have* been replaced by a preferred codon encoding the same amino acid, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said protein in a mammalian host cell at a level which is at least 110% of that expressed by said natural gene in an in vitro mammalian cell culture system under identical conditions.

12. A synthetic gene encoding a lentiviral protein wherein at least [one non-preferred or less preferred codon in the natural gene encoding said protein has] *50% of the non-preferred codons and less preferred codons present in said natural gene have* been replaced by a preferred codon encoding the same amino acid, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said lentiviral protein in a mammalian host cell at a level which is at least 110% of that expressed by said natural gene in an in vitro mammalian cell culture system under identical conditions.

17. A method for preparing a synthetic gene encoding a protein normally expressed by mammalian cells, comprising identifying non-preferred and less preferred codons in the natural gene encoding said protein and replacing [one or more] *at least 50%* of said non-preferred and less preferred codons with a preferred codon encoding the same amino acid as the replaced codon, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said protein in a mammalian host cell at a level which is at least 110% of that expressed by said natural gene in an in vitro mammalian cell culture system under identical conditions.

18. A method for preparing a synthetic gene encoding a lentiviral protein, comprising identifying non-preferred and less preferred codons in the natural gene encoding said lentiviral protein and replacing [one or more] *at least 50%* of said non-preferred and less preferred codons with a preferred codon encoding the same amino acid as the replaced codon, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consiting of ggg, att, ctc, tcc, and gtc, said non-preferred codons being all codons other than said preferred codons and said less preferred codons, wherein said synthetic gene permits the expression of said lentiviral protein in a mammalian host cell at a level which is at least 110% of that expressed by said natural gene in an in vitro mammalian cell culture system under identical conditions.

*19. The method of claim 17 wherein at least 10% of the codons in said natural gene are non-preferred codons.*

*20. The method of claim 17 wherein at least 50% of the codons in said natural gene are non-preferred codons.*

*21. The method of claim 17 wherein at least 90% of the non-preferred codons and less preferred codons present in said natural gene have been replaced by preferred codons.*

*22. The method of claim 17 wherein said protein is a human protein.*

*23. A synthetic gene encoding a human protein wherein at least one non-preferred or less preferred codon in the natural gene encoding said protein has been replaced by a preferred codon encoding the same amino acid, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said protein in a mammalian host cell at a level which is at least 110% of that expressed by said natural gene in an in vitro mammalian cell culture system under identical conditions.*

*24. The synthetic gene of claim 23 wherein at least 10% of the codons in said natural gene are non-preferred codons.*

*25. The synthetic gene of claim 23 wherein at least 50% of the codons in said natural gene are non-preferred codons.*

*26. The synthetic gene of claim 23 wherein at least 90% of the non-preferred codons and less preferred codons present in said natural gene have been replaced by preferred codons.*

*27. A method for preparing a synthetic gene encoding a human protein normally expressed by mammalian cells, comprising identifying non-preferred and less preferred codons in the natural gene encoding said protein and replacing one or more of said non-preferred and less preferred codons with a preferred codon encoding the same amino acid as the replaced codon, said preferred codons being selected from the group consisting of gcc, cgc, aac, gac, tgc, cag, ggc, cac, atc, ctg, aag, ccc, ttc, agc, acc, tac, and gtg, said less preferred codons being selected from the group consisting of ggg, att, ctc, tcc, and gtc, said non-preferred codons being all codons other than said preferred codons and said less preferred codons, wherein said synthetic gene permits the expression of said protein in a mammalian host cell at a level which is at least 110% of that expressed by said natural gene in an in vitro mammalian cell culture system under identical conditions.*

*28. The method of claim 27 wherein at least 10% of the codons in said natural gene are non-preferred codons.*

*29. The method of claim 27 wherein at least 50% of the codons in said natural gene are non-preferred codons.*

*30. The method of claim 27 wherein at least 90% of the non-preferred codons and less preferred codons present in said natural gene have been replaced by preferred codons.*

* * * * *

US005786464C2

(12) EX PARTE REEXAMINATION CERTIFICATE (9821st)

United States Patent

(10) Number: US 5,786,464 C2
(45) Certificate Issued: Aug. 29, 2013

Seed et al.

(54) OVEREXPRESSION OF MAMMALIAN AND VIRAL PROTEINS

(75) Inventors: Brian Seed, Boston, MA (US); Jurgen Haas, Munich (DE)

(73) Assignee: National Institutes of Health (NIH), U.S. Dept. of Health and Human Services (DHHS), Washington, DC (US)

Reexamination Request:
No. 90/012,335, Jun. 22, 2012

Reexamination Certificate for:

| | |
|---|---|
| Patent No.: | **5,786,464** |
| Issued: | **Jul. 28, 1998** |
| Appl. No.: | **08/324,243** |
| Filed: | **Sep. 19, 1994** |

Reexamination Certificate C1 5,786,464 issued Apr. 24, 2012

Certificate of Correction issued Nov. 9, 1999
Certificate of Correction issued Sep. 25, 2012

(51) Int. Cl.

| | |
|---|---|
| ***C07K 14/16*** | (2006.01) |
| ***C12N 15/85*** | (2006.01) |
| ***C07K 14/005*** | (2006.01) |
| ***C07K 14/435*** | (2006.01) |
| ***C12N 15/67*** | (2006.01) |

(52) U.S. Cl.
CPC ......... *C07K 14/005* (2013.01); *C07K 14/43595* (2013.01); *C12N 15/67* (2013.01); *C12N 2740/16122* (2013.01)
USPC ..... 536/23.5; 435/252.3; 435/69.1; 435/91.5; 536/23.72

(58) Field of Classification Search
None
See application file for complete search history.

(56) References Cited

To view the complete listing of prior art documents cited during the proceeding for Reexamination Control Number 90/012,335, please refer to the USPTO's public Patent Application Information Retrieval (PAIR) system under the Display References tab.

*Primary Examiner* — Shri Ponnaluri

(57) ABSTRACT

The invention features a synthetic gene encoding a protein normally expressed in mammalian cells wherein at least one non-preferred or less preferred codon in the natural gene encoding the mammalian protein has been replaced by a preferred codon encoding the same amino acid.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 12, 13 and 18 is confirmed.

Claim 8 was previously cancelled.

Claims 1-7, 9-11, 17 and 19-30 are cancelled.

Claims 14-16 were not reexamined.

* * * * *